US009651508B2

(12) United States Patent
Bischof et al.

(10) Patent No.: US 9,651,508 B2
(45) Date of Patent: May 16, 2017

(54) THERMAL CONTRAST ASSAY AND READER

(71) Applicant: Regents of the University of Minnesota, Minneapolis, MN (US)

(72) Inventors: John C. Bischof, St. Paul, MN (US); Zhenpeng Qin, Minneapolis, MN (US); Warren Chan, Ontario (CA); Taner Akkin, Minneapolis, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 94 days.

(21) Appl. No.: 14/375,294

(22) PCT Filed: Jan. 30, 2013

(86) PCT No.: PCT/US2013/023839
§ 371 (c)(1),
(2) Date: Jul. 29, 2014

(87) PCT Pub. No.: WO2013/116333
PCT Pub. Date: Aug. 8, 2013

(65) Prior Publication Data
US 2014/0377770 A1 Dec. 25, 2014

(51) Int. Cl.
*G01N 25/48* (2006.01)
*G01N 21/84* (2006.01)
*G01N 33/558* (2006.01)

(52) U.S. Cl.
CPC ..... *G01N 25/4806* (2013.01); *G01N 21/8483* (2013.01); *G01N 25/48* (2013.01); *G01N 33/558* (2013.01); *G01N 2021/8488* (2013.01)

(58) Field of Classification Search
None
See application file for complete search history.

(56) References Cited

U.S. PATENT DOCUMENTS 4,094,647 A 6/1978 Deutsch et al.
4,313,734 A 2/1982 Leuvering
(Continued)

FOREIGN PATENT DOCUMENTS

CN 101368907 A 2/2009
EP 1 225 44 7/2002
(Continued)

OTHER PUBLICATIONS

Office Action issued in corresponding Chinese Patent application No. 201380016094.5 mailed on Feb. 29, 2016.
(Continued)

*Primary Examiner* — Rebecca Martinez
(74) *Attorney, Agent, or Firm* — Westman, Champlin & Koehler, P.A.; Visala Goswitz

(57) ABSTRACT

Assays used in conjunction with a thermal contrast reader are disclosed. In the assay, the test strip includes materials that can develop a thermal response if a target analyte is present in a sample. The thermal contrast reader includes housing having an opening to receive the test strip at a test location, an energy source directed at the test location and a heat sensor directed at the test location. The heat sensor is configured to sense heating of the test strip upon activation of the heat source at the test location, if the target analyte is present in the sample. The heat sensor can provide sensor output using diagnostic circuitry coupled to the sensor output and configured to provide a diagnostic output. The diagnostic output can indicate the diagnostic condition of the patient as a function of the sensor output. The present disclosure also includes methods of detecting target analytes and kits comprising lateral flow assays and thermal contrast reader.

8 Claims, 16 Drawing Sheets

(56) References Cited

U.S. PATENT DOCUMENTS

| | | | |
|---|---|---|---|
| 4,857,453 | A | 8/1989 | Ullman et al. |
| 5,073,484 | A | 12/1991 | Swanson et al. |
| 5,559,041 | A | 9/1996 | Kang et al. |
| 5,571,726 | A | 11/1996 | Brooks, Jr. et al. |
| 5,578,577 | A | 11/1996 | Ching et al. |
| 5,591,645 | A | 1/1997 | Rosenstein |
| 6,187,598 | B1 | 2/2001 | May et al. |
| 6,352,862 | B1 | 3/2002 | Davis et al. |
| 6,485,982 | B1 | 11/2002 | Charlton |
| 7,297,529 | B2 | 11/2007 | Polito et al. |
| 7,314,763 | B2 | 1/2008 | Song et al. |
| 7,371,582 | B2 | 5/2008 | Nahm et al. |
| 8,021,848 | B2 | 9/2011 | Straus |
| 8,034,397 | B2 | 10/2011 | Yang et al. |
| 8,105,843 | B2 | 1/2012 | Buchanan |
| 8,128,871 | B2 | 3/2012 | Petruno et al. |
| 8,153,444 | B2 | 4/2012 | Kirkegaard et al. |
| 2003/0119202 | A1 | 6/2003 | Kaylor et al. |
| 2003/0143580 | A1 | 7/2003 | Straus |
| 2004/0180369 | A1 | 9/2004 | Franzen et al. |
| 2008/0095714 | A1* | 4/2008 | Castella ............... A61B 5/0066 424/9.3 |
| 2008/0102473 | A1 | 5/2008 | Fouquet et al. |
| 2009/0211345 | A1 | 8/2009 | Nahm et al. |
| 2010/0136566 | A1 | 6/2010 | Mehra et al. |
| 2012/0258881 | A1 | 10/2012 | Schwartz et al. |

FOREIGN PATENT DOCUMENTS

| | | |
|---|---|---|
| EP | 1225442 A2 | 7/2002 |
| EP | 1 933 147 | 8/2011 |
| WO | WO 00/31539 | 6/2000 |
| WO | WO 03/060461 | 7/2003 |
| WO | WO 03/073817 | 9/2003 |
| WO | WO 2004/092715 | 10/2004 |
| WO | WO 2007/090058 | 8/2007 |
| WO | WO 2007/135613 | 11/2007 |
| WO | WO 2008/067079 | 6/2008 |
| WO | WO 2009/152209 | 12/2009 |

OTHER PUBLICATIONS

"A Colorimetric Gold Nanoparticle Sensor to Interrogate Biomolecular Interactions in Real Time on a Surface", by Nath et al., Analytical Chemistry, vol. 74, No. 3, Feb. 1, 2002.

"A Fast and Sensitive Quantitative Lateral Flow Immunoassay for Cry1Ab Based on a Novel Signal Amplification Conjugate", by Chen et al., Sensors, 2012.

"A Lateral Flow Assay for Quantitative Detection of Amplified HIV-1 RNA", by Rohrman et al., PLOS ONE, vol. 7, Issue 9, Sep. 2012.

"Photothermal Multispectral Image Cytometry for Quantitative Histology of Nanoparticles and Micrometastasis in Intact, Stained and Selectively Burned Tissues", by Nedosekin et al., Cytometry Part A, 2010.

"Detection of DNA Hybridization on Indium Tin Oxide Surfaces", by Moses et al., Sensors and Actuators B, 2007.

"Development of Gold Nanorod Lateral Flow Test for Quantitative Multi-Analyte Detection", by Venkataramasubramani et al., IFMBE Proceedings 24, 2009.

"Direct Measurements of Heating by Electromagnetically Trapped Gold Nanoparticles on Supported Lipid Bilayers", by Bendix et al., ACSNANO, vol. 4, No. 4, Apr. 6, 2010.

"Discerning Trends in Multiplex Immunoassay Technology with Potential for Resource-Limited Settings", by Gordon et al., Clinical Chemistry 58:4, 2012.

"Gold and Silican-Coated Gold Nanoparticles as Thermographic Labels for DNA Detection", by Cerruti et al., Analytical Chemistry, vol. 78, No. 10, May 15, 2006.

"Enhancement of the Detection Limited for Lateral Flow Immunoassays: Evaluation and Comparison of Bioconjugates", by Linares et al., Journal of Immunological Methods, 2012.

"Lateral Flow (immuno)assay: its Strengths, Weaknesses, Opportunities and Threats. A Literature Survey", by Posthuma-Trumpie et al., Anal Bioanal Chem., 2009.

"Gold Nanoparticles in Biology and Medicine: Recent Advances and Prospects", by Dykman et al., Acta Naturae, vol. 3, No. 2, 2011.

"Room-Temperature Detection of a Single Molecule's Absorption by Photothermal Contrast", by Yorulmaz et al., Science, vol. 330, Oct. 15, 2010.

"Significantly Improved Analytical Sensitivity of Lateral Flow Immunoassays by Thermal Contrast", by Qin et al., Angew Chem Int Ed Engl., Apr. 27, 2012.

"Chapter 1 Evolution in Lateral Flow-Based Immunoassay Systems", by O'Farrell, Lateral Flow Immonoassay, 2009.

"Chapter 5 Colloidal Gold and Other Labels for Lateral Flow Immunoassays", by Chun, Lateral Flow Immunoassay, 2009.

"Chapter 9 Handheld and Portable Reader Devices for Lateral Flow Immunoassays", by Faulstich et al., Lateral Flow Immunoassay, 2009.

"Thermophysical and Biological Responses of Gold Nanoparticle Laser Heating", by Qin et al., Chem. Soc. Rev., 2012.

"Ultrasensitive Heterogeneous Immunoassay Using Photothermal Deflection Spectroscopy. 2. Quantitation of Ultratrace Carcinoembryonic Antigen in Human Sera", by Kimura et al., Analytical Chemistry, vol. 68, No. 17, Sep. 1, 1996.

Notification of Transmittal of the International Search Report and the Written Opinion of the International Searching Authority, or the Declaration, PCT/US2013/023839, dated Sep. 4, 2013.

* cited by examiner

Synthesized
29.8nm (±2.9nm)

hCG dipstick
D=32.2nm (±6.4nm)

CM* dipstick
D=25.3nm (±5.5nm)

*CM: cryptococcal meningitis

THERMAL CONTRAST ASSAY AND READER

CROSS-REFERENCE TO RELATED APPLICATION

This Application is a Section 371 National Stage Application of International Application No. PCT/US2013/023839, filed Jan. 30, 2013 and published as WO 2013/116333 on Aug. 8, 2013, in English, the contents of which are hereby incorporated by reference in their entirety.

FIELD

The present invention relates to assays and readers for detecting analytes in a sample. More specifically, the present invention relates to assays and readers that operate based upon thermal contrast.

BACKGROUND

LFA (lateral flow assay, or lateral flow immunoassay, also called rapid diagnostic test—RDT, or bioassays) technology has found widespread use both in and out of laboratory settings. In a typical assay, a fluid sample from a patient is applied to a test strip. The sample interacts with chemicals on the test strip causing the strip to optically change characteristics. The visual indicator may be observed by a person, for example, using a home pregnancy test. However, more accurate readings can be obtained using an assay reader. Such a reader may, for example, include a sensitive optical sensor that is capable of sensing optical variations more accurately and in a more repeatable manner than a human viewer. One example of a typical assay reader is shown in U.S. Pat. No. 7,297,529, to Polito et al., issued Nov. 20, 2007.

The ability to rapidly identify diseases enables prompt treatment and improves outcomes. This possibility has increased the development and use of rapid point-of-care diagnostic devices or systems that are capable of biomolecular detection in both high-income and resource-limited settings. LFAs are inexpensive, simple, portable and robust, thus making LFAs commonplace in medicine, agriculture, and over-the-counter personal use, such as for pregnancy testing. LFAs are also widely used for a number of infectious diseases, such as malaria, AIDS-associated cryptococcal meningitis, pneumococcal pneumonia, and recently tuberculosis.

Although the analytical performance of some LFAs are comparable to laboratory-based methods, the analytical sensitivity (alternatively called limit of detection) of most LFAs is in the mM to µM range, which is significantly less sensitive than other molecular techniques such as enzyme-linked immmunoassays (ELISAs). As a consequence, LFAs are not particularly useful for early detection in a disease course when there is low level of antigen. Research has focused on developing microfluidics, biobarcodes and enzyme-based assay technologies to obtain higher sensitivity in antigen detection since these techniques may potentially detect in the nM to pM range. However, all of these methods are still in the development stage and have not been demonstrated for adoption in a reliable, cost-effective manner to use in a point-of-care site by an end user.

As is now well known, the optical, thermal and electrical properties of materials change dramatically in the nanoscale. In particular, the enhanced photothermal signature of metal nanoparticles have been utilized for: thermal ablation of malignant tumors, detecting circulating tumor cells, photothermal gene transfection, enhancing the therapeutic efficiency of chemotherapeutics, and for tracking the transport of nanoparticles within cells.

SUMMARY

In one aspect, the present invention relates to a thermal contrast assay reader. The thermal contrast assay reader includes an energy source, a sensor, I/O circuitry and an opening to receive an assay strip. The reader is configured to convert the sensor results to an output signal upon activation of the energy source onto the test region of the assay strip.

In another aspect, the present invention relates to an assay kit comprising an assay system. The assay kit comprising a sample pad, a test strip, nanoparticles conjugated to an analyte binding molecule, a test region, a control region and an absorbent pad configured for fluid communication when a sample is applied. The kit also includes a thermal contrast assay reader.

In a further aspect, the present invention relates to a method of detecting analytes in a sample comprising exposing the test region of a test strip in an assay system to an energy source after contacting the test strip of the assay system with a sample. The sample moves through the test strip by capillary action and the assay system comprises nanoparticles conjugated to analyte binding molecule that bind the analyte in the sample and a test region comprising capture molecules. The method also includes measuring the heat generated in the test region by a sensor to detect the presence or absence of the analyte in the test region.

DETAILED DESCRIPTION

Figure 1:
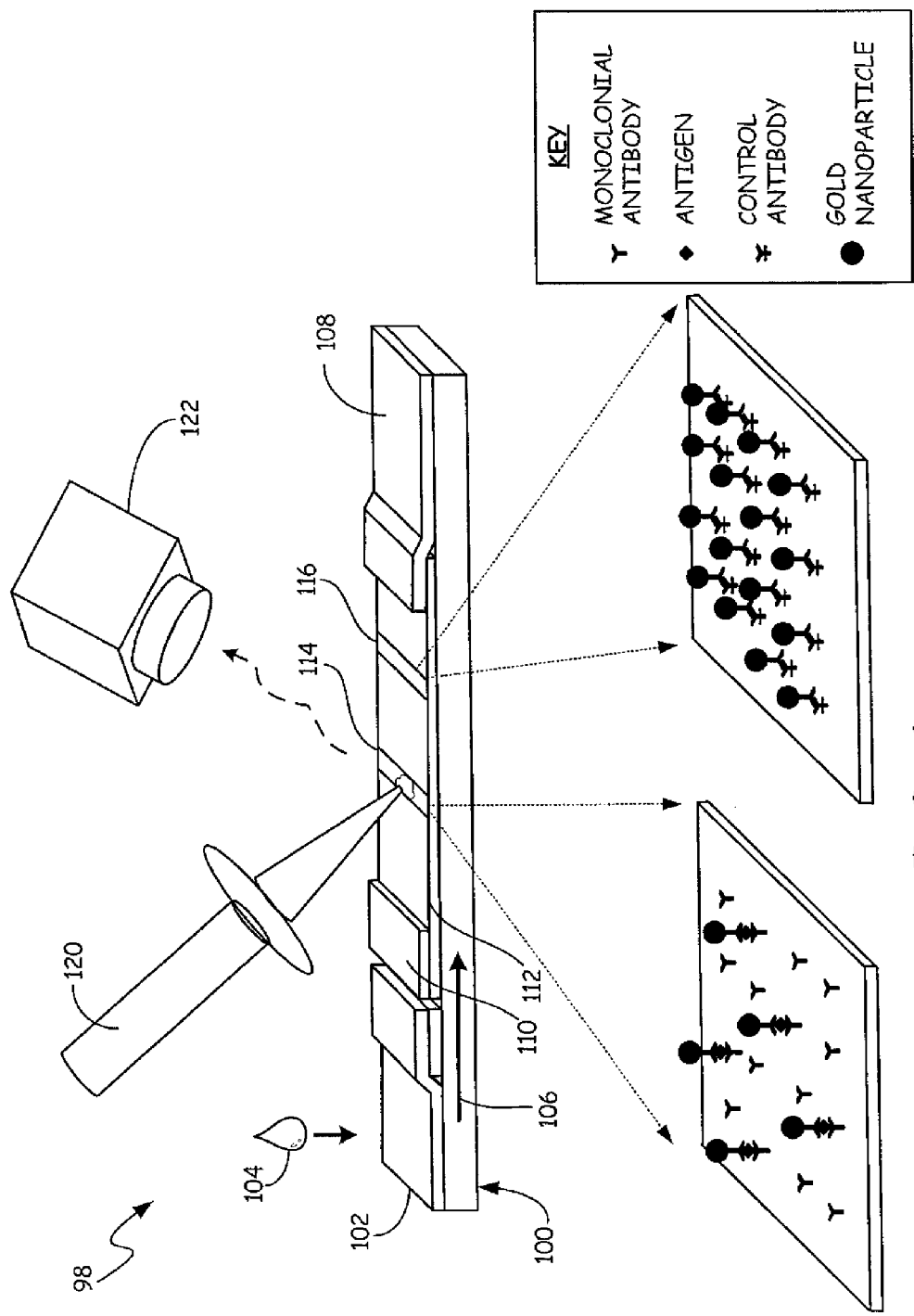
FIG. 1 is a simplified diagram showing a lateral flow assay test strip and reader system.

The present invention relates to assay systems that are used in conjunction with a thermal contrast reader. The present invention also relates to methods for detecting analytes in a sample using the thermal contrast assay and reader systems. The present invention includes an assay test strip that exhibits a thermal characteristic that changes in response to exposure to specific target compounds that may be present in a sample. The present invention includes a reader for reading the thermal properties of such a test strip. Aspects of the present invention are discussed below in greater detail.

Thermal contrast assay systems are assays that are configured to work in conjunction with a thermal contrast reader. A thermal contrast assay system can be advantageously used to detect analytes in samples at much lower concentrations than assays using visual readers. The thermal contrast assay system can be a highly sensitive detection system for analytes in a variety of samples. This advantageously enables detection of diseases or conditions at a much earlier stage than comparable LFAs using visual detection methods. In addition, the simplicity of the method enables an end-user to use the system with ease and accuracy. This system can be highly amenable to point-of-care facilities and resource-limited settings. Embodiments described herein relate to thermal contrast assay systems that can be used to extend the sensitivity, dynamic range, and quantification of clinically used LFAs.

The present description also includes a kit wherein the kit includes a thermal contrast reader and an assay system described herein. The kit can be used by an end user to process a desired sample using the assay system and then to detect the target analyte and/or the quantity of the target analyte using the thermal contrast reader. The kit may include instructions related to the use of the kit.

The present description generally relates to laser excitation of nanoparticles, although it is understood that other embodiments with electromagnetic excitation are also within the scope of this invention. Laser (or light) excitation of nanoparticles as referred to herein relates to excitation of nanoparticles to produce heat that can be read by an infrared or other heat sensor with the understanding that other embodiments are also possible and within the scope of this invention. Diagnostic circuitry coupled to the sensor output is configured to provide a diagnostic output indication of a diagnostic condition of the patient as a function of the sensor output.

The assay systems described herein can be used to detect target analytes in a sample using nanoparticles conjugated with analyte binding molecules. Specifically, nanoparticles in assays can be used efficiently to convert incoming light to heat. In the assays, a membrane is contacted with a sample potentially containing an analyte. As the sample moves through the membrane, generally by capillary action, nanoparticles conjugated with the analyte binding molecules bind the target analyte to form a nanoparticle/analyte complex. "Nanoparticle/analyte complex" as used herein refers to nanoparticles conjugated to analyte binding molecules that have bound analyte from the sample. The nanoparticle/analyte complex continues to move through the membrane toward a test region containing capture molecules that bind the desired analyte. The nanoparticle/analyte complex is bound by the capture molecules and retained in the test region. A thermal contrast reader described herein can then be used to detect the presence or absence of the analyte. In addition, the thermal contrast reader can also quantitate the amount of analyte present in the test region and consequently, the sample. The thermal contrast reader generally includes a heat source and a heat sensor configured as described below.

An assay system, i.e. an LFA, generally includes a sample pad, a membrane, nanoparticles conjugated to an analyte binding molecule and capture molecules for the analyte. The LFA system may also include a conjugate pad, an absorbent pad, a backing, a test region, a control region and/or combinations of all of these components. The test region generally includes analyte capture molecules. The control region can include a control molecule such as a control antibody. The conjugate pad generally includes the nanoparticles conjugated to the analyte binding molecules.

"Membrane" as used herein refers to a test device or strip that employs a membrane and one or more reagents to detect the target analyte in the sample. "Membrane" and "test strip" may be used interchangeably.

Assays that can be used in conjunction with the thermal contrast reader include lateral flow assays. A variety of configurations for conducting lateral flow assays are known in the art and described, for example, in U.S. Patent Publication US 2003/0119202 by Kaylor et al. and US Patent Publication No. US 2010/0136566 by Mehra et al. and are incorporated herein by reference. FIG. 1 illustrates one exemplary embodiment and other configurations for conducting lateral flow assays are known in the art and also within the scope of the invention.

FIG. 1 is a simplified diagram showing an exemplary embodiment of a lateral flow assay test and reader system 98 in accordance with the present invention. A test strip 100 includes a sample pad 102 that is configured to receive a sample 104 from a patient. Capillary action causes the sample 104 to flow from the sample pad 102 in the direction indicated by arrow 106 towards absorbent pad 108. Sample 104 flows through a conjugate pad 110 and through a membrane 112 until it reaches a test region 114. A separate control region 116 is also provided. Test strip 100, sample pad 102, absorbent pad 108, conjugate pad 110, test region 114 and control region 116 are all in fluid communication. "Fluid communication" as used herein refers to the ability of liquid to flow or travel between the stated materials or surfaces.

As illustrated in the inset of FIG. 1, an exemplary embodiment of the test region can include gold nanoparticles associated with a monoclonal antibody bonded with the antigen at test region 114. The amount of bonded gold nanoparticles bonded in test region 114 can be determined by applying energy 120 causing heating of the test region 114. A thermal sensor 122 directed at the test region 114 measures the heating of the test region 114 that is related to the amount of nanoparticles and therefore the amount of antigens present in the test region 114. As explained below in more detail, this can be used to diagnose a condition of the patient. The energy 120 can be any form of energy that causes heating of test region 114. Energy source 120 and sensor 122 may be housed in one unit. Alternatively, they may be housed separately.

In the embodiment depicted in the FIG. 1 inset, the analyte binding molecules and capture molecules are shown to be monoclonal antibodies. The analyte binding molecule and the capture molecules may be the same type of molecule, i.e. an antibody. In such instances, they preferably bind the analyte at different sites, in other words, the analyte binding molecule and the capture molecule preferably do not bind to the same site or epitope of the analyte. Alternatively, the analyte binding molecule and the capture molecule can be two different molecules, but both capable of binding the analyte at different sites.

In the exemplary embodiment discussed above, antibody-coated GNPs are moved within a nitrocellulose strip through capillary action after the strip has been dipped or contacted with a clinical specimen. When present, the target antigen binds to monoclonal antibody-coated GNPs. This bound complex stops wicking up the "dipstick" when captured by an antibody on the membrane that recognizes the antigen-antibody-GNP complex. This leads to accumulation of GNPs at the test region 114 of the LFA, creating a positive test result. GNPs have been used for LFAs because their size can be designed to migrate through the pores of the membrane 112; GNPs can be coated with antibodies easily; and GNPs have a strong interaction with visible light thus producing deep color that is easily visualized. GNPs that have strong interaction with light at other light wavelengths may be used for thermal contrast detection, for instance gold nanorod with maximum light absorption in the near infrared.

Figure 2A:
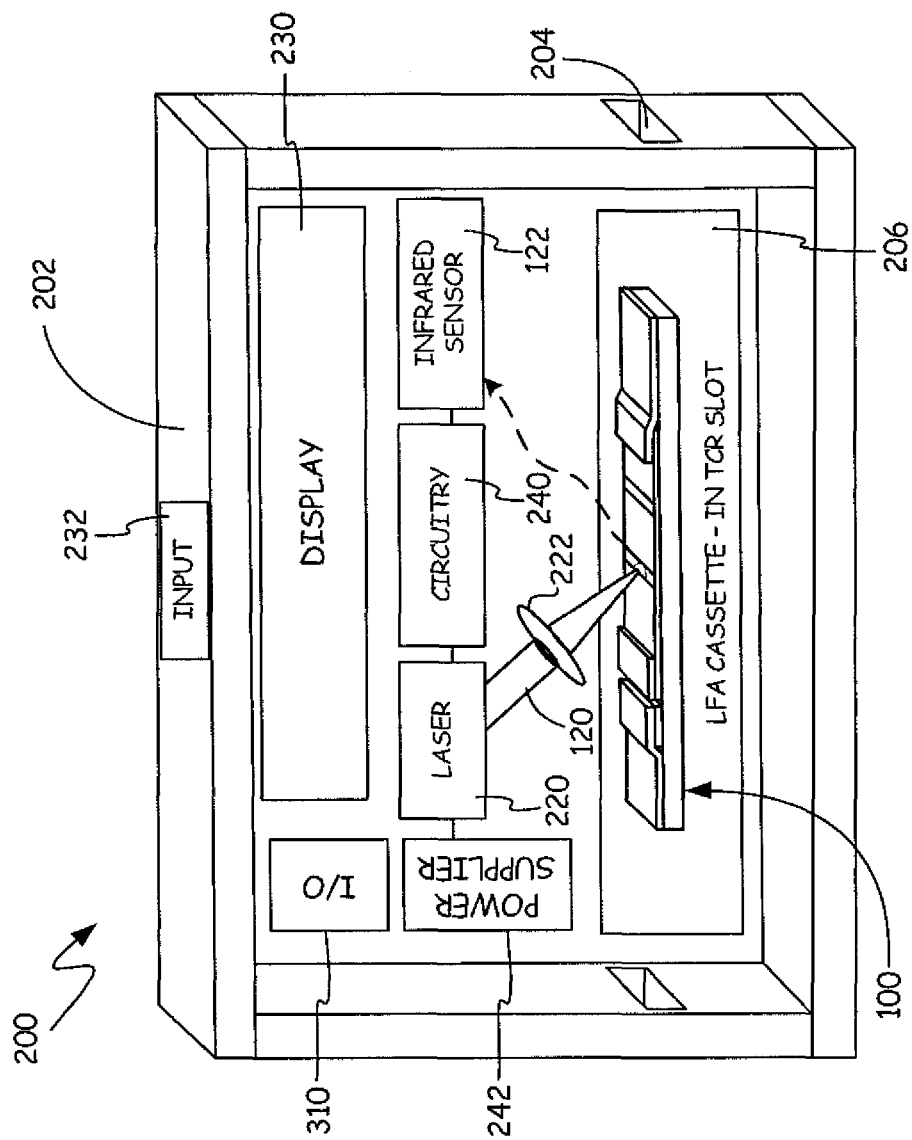
FIG. 2A is a simplified block diagram of a portable assay reader.

FIG. 2A is a simplified block diagram of a portable assay reader 200 in accordance with one example embodiment of the present invention. Reader 200 includes a housing 202 having an opening 204 therein configured to receive the LFA 100 in a slot or holder 206. In FIG. 2A, a laser 220 generates energy 120 directed to the test region of the LFA 100. In FIG. 2A, the energy can be, for example, visible or near infrared light that is focused on the test region using an optional lens 222. As discussed herein, visible or near infrared light directed at nanoparticles can cause heating of the nanoparticles. This is detected with a sensor 122 such as an infrared sensor. The results of the test can be displayed on a display 230 which can comprise for example, LCD display. The display can provide a quantitative output or a qualitative output such as a simple pass/fail indication. An optional user input 232 is provided. For example, this input can be a single button allowing an operator to initialize a test, or can be a more complex input such as a numerical keypad or of a numeric keypad allowing an operator to update parameters such as threshold values used by the device 200. The input 232 can be an overlay on display 230 to provide a touch-screen.

Operation of device 200 is controlled by electronic circuitry 240 as described below in more detail. This may include, for example, a microprocessor, analog-to-digital converters, I/O circuitry, etc. A power source 242 is provided. Preferably, the power source 242 is a portable power source such as a battery or the like. The power source may optionally be rechargeable either through connection to another electrical source or using a solar cell or the like.

Additionally, device 200 includes input/output (I/O) circuitry 310 that is described below in more detail. I/O circuitry 310 allows data collected by the device 200 to be transmitted or otherwise provided to other devices. For example, test results can be collected and transmitted to a central location or cloud server for subsequent evaluation.

Figure 2B:
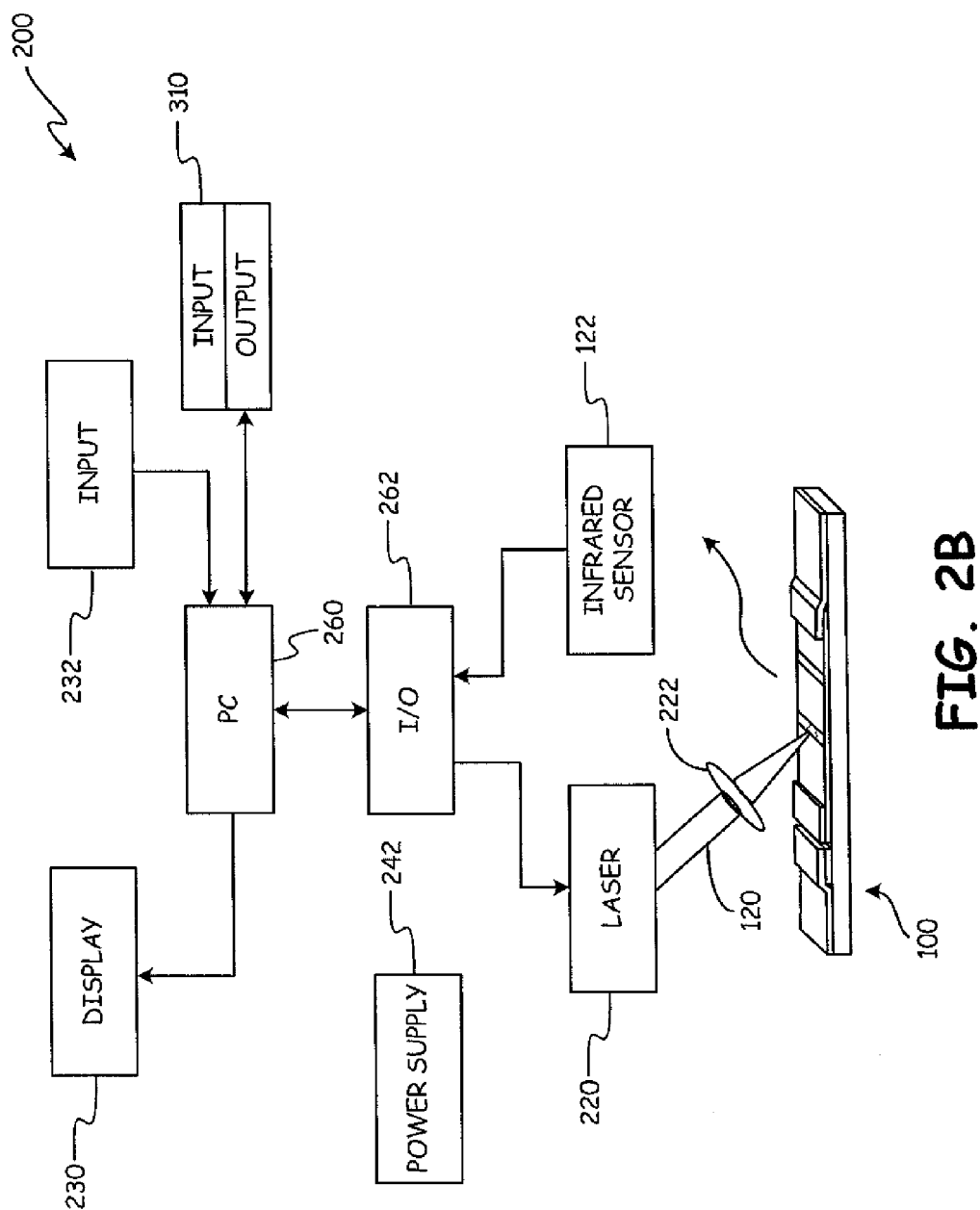
FIG. 2B is simplified block diagram of a bench top assay reader.

FIG. 2B is a simplified block diagram of assay reader 200 configured in a "bench top" configuration. In the configuration of FIG. 2B, a computer identified as PC is used to perform the testing. PC 260 couples to laser 220 and infrared sensor 122 through I/O circuitry 262. I/O circuitry 262 can include, for example, digital-to-analog converters, analog-to-digital converters, switchable outputs, etc. Typically, the PC 260 shown in FIG. 2B will have more computing power than that is available in a portable device. This may allow additional testing or more advanced testing to be performed.

Although any appropriate components may be employed, in one preferred embodiment, the source 220 comprises a laser, for example a 532 nm green laser (i.e. LRS-0532-PFM_00200-03, LaserGlow Technologies Inc). Focusing optics 222 can comprise for example a plano-convext focusing lens. A suitable infrared sensor includes an infrared camera (A20 or E30, FLIR Inc) or infrared sensor (MLX90614, Melexis). However, the present invention is not limited to this configuration.

Figure 3:
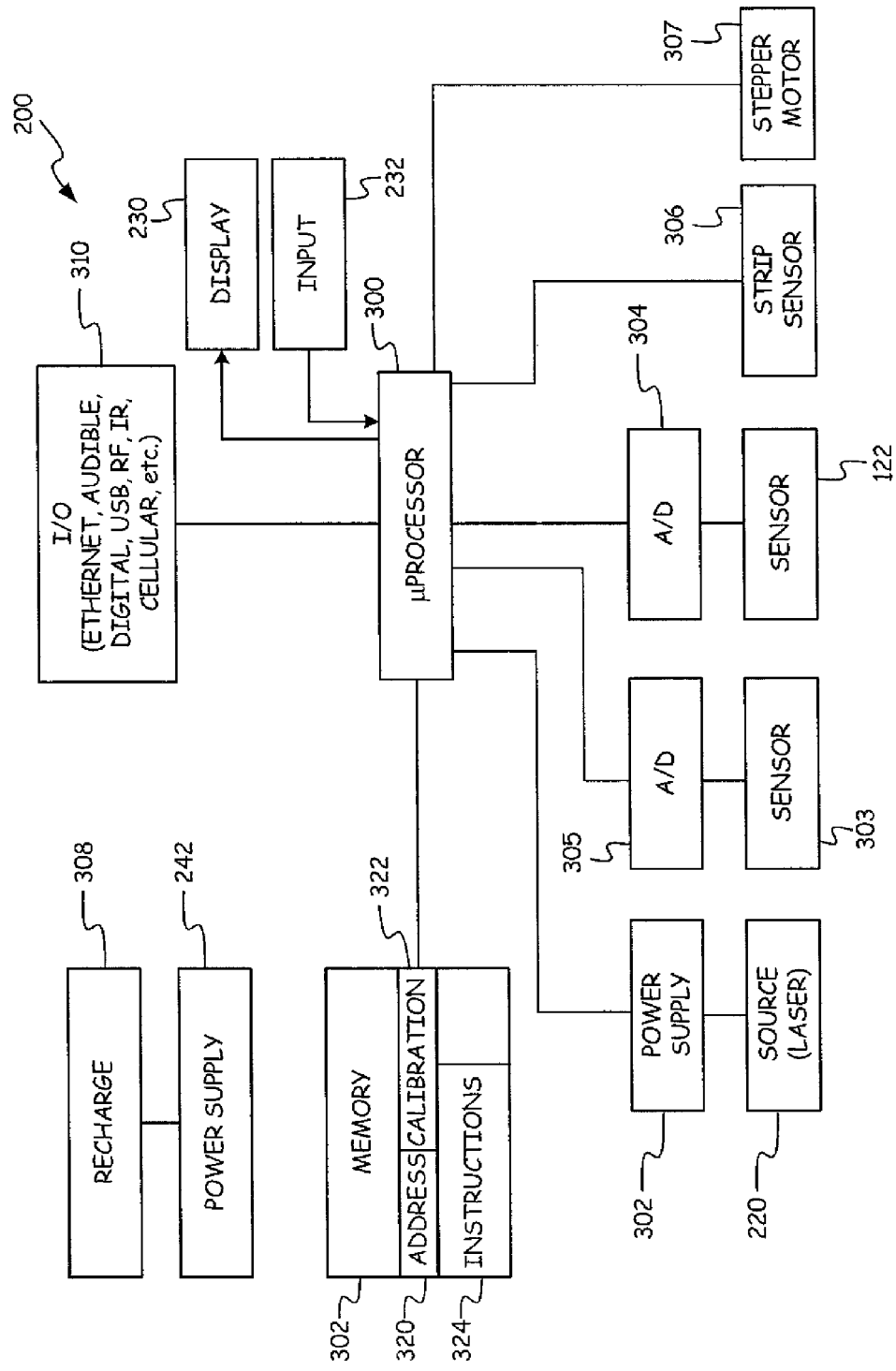
FIG. 3 is a simplified block diagram of the assay reader of FIG. 2A.

FIG. 3 is a simplified block diagram of device 200 and includes a microprocessor 300 operating in accordance with instructions stored in a memory 302. Microprocessor 300 controls the energy source 220 by activating energy source power supply 302. The heating of the LFA (not shown in FIG. 3) is detected by heat sensor 122 that provides an output to an analog-to-digital converter 304. An optional strip sensor 306 is provided. Strip sensor 306 can be configured to detect the presence of LFA 100 in slot 206 thereby allowing the microprocessor 300 to activate the energy source 220 and begin the test.

FIG. 3 shows an optional recharge circuit 308 connected to power supply 242. This may allow the power supply 242 to be recharged, for example, using an external power source, a solar cell, a mechanical crank, etc.

Input/output circuitry 310 is also illustrated coupled to microprocessor 300. This may include any type of input or output device including a display, keyboard or manual input, audible output, digital output such as a USB or Ethernet connection, an RF (radio frequency) or IR (infrared) input and/or output, a cellular data connection, an Ethernet connection, etc. Example RF connections include but are not limited to BLUETOOTH® connections or other short distance communication techniques, WIFI connections, or others. Cellular phone connections allow the device to communicate using a cellular phone network for communicating data and/or providing optional voice communication. The data may include the test results and geographic information (GPS location) to collect spatiotemporal information on infectious diseases.

The use of I/O 310 allows data collected by device 200 to be sent to another location. For example, when used in the field, device 200 can transmit test results back to a central database. This transmission can be through any appropriate technique. For example, data can be sent through an Internet connection, over a cellular network, etc. The connection may require a physical wired connection or may occur wirelessly using WIFI, Bluetooth, etc. Additionally, the I/O can be used to update information stored in the memory 302. For example, programming instructions, calibration information or other data may be updated. The I/O 310 may also be used to communicate with an operator from a remote location using display 230 and/or input 232.

During operation, a LFA 100 (not shown in FIG. 3) is placed within housing 202, for example through slot 204 (shown in FIG. 2). The test process is initiated by microprocessor 300 in response to a signal from the strip sensor 306, or some other trigger such as a manual input using input/output circuitry 310. In one configuration, an optional stepper motor 307 is provided and controlled by the microprocessor 300. The stepper motor 307 can be used to automate the movement of the LFA 100 within the device 200. The multiple strip sensors 306, or other configurations can be used if it is desired to monitor the location of the LFA 100 within the device 200. This causes the microprocessor 300 to apply power to the energy source 220 thereby heating the LFA 100. The heating response is sensed by sensor 122 and converted into a digital signal using an analog-to-digital signal converter 304. Based upon this digitized signal, the microprocessor 300 provides an output using input/output circuitry 310 that is indicative of the test results.

Additionally, FIG. 3 shows a feedback sensor 303 that is arranged in the path of source 220 in order to sense the strength of the applied energy. The output from the feedback sensor 303 is provided to the processor 300 through an analog to digital converter 305. For example, sensor 303 can be a light sensor to sense the intensity of the output from a laser 220. This information can be used to calibrate operation of the device and calibrate the sensed heating. Further, the feedback can be used for diagnostic purposes in order to detect a source 220 that is putting out a weak signal or has failed completely.

Memory 302 is used by microprocessor for short and long-term storage of information. For example, addressing information 320 of the device 200 can be stored in memory 302. This address may be, for example, an address that uniquely or semi-uniquely identifies the device 200 and may include, but is not limited to an Internet protocol (IP) address, a Mac address, or other address format. The memory 302 may also be used to store calibration information that can be used to calibrate the data received from sensor 122. The calibration information can be determined in any number of ways including, for example, during manufacture of the device, input using circuitry 310, or based upon a calibration performed using a LFA 100, for example, using calibration region 116 shown in FIG. 1. This calibration information can provide a baseline or other type of offset to the readings provided by the sensor 122. Memory 302 also includes operating instructions 324 which are used to control operation of the microprocessor 300.

Figure 4A:
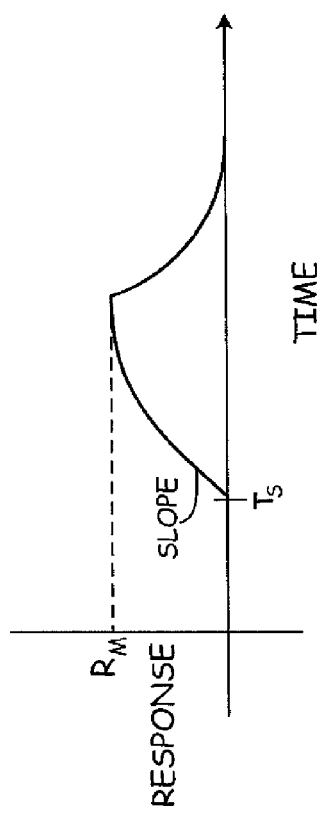
FIGS. 4A and 4B are graphs illustrating the thermal response of a LFA versus time.
Figure 4B:
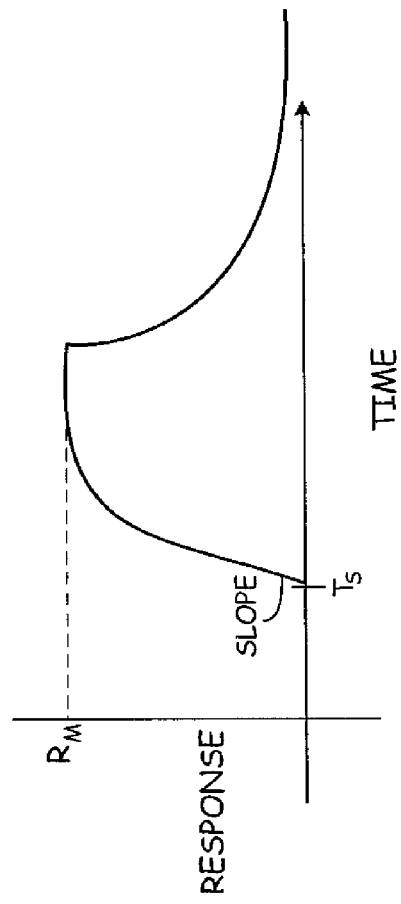

FIGS. 4A and 4B are graphs which illustrate the heating response of LFA 100 when energy 120 is applied, $T_S$. The amount of heating reaches a maximum indicated by $R_M$. Further, as illustrated in FIGS. 4A and 4B, the response has a slope which begins at its steepest rise and slowly levels off to the maximum level $R_M$. Microprocessor 300 operates as diagnostic circuitry by analyzing the heating response to the applied energy signal. For example, a simple threshold level can be used in which the maximum response is compared to a threshold level. This can be provided as an output, for example a "pass/fail" output based upon the comparison. Further, a quantitative output can be provided based upon the maximum response level. This quantitative output can illustrate the amount of gold nanoparticles that have been captured at the test location 114 (shown in FIG. 1). This can be correlated to, for example, the amount of antigen and therefore the progression of a disease in the patient.

In one aspect of the present invention, the diagnostics are based upon the profile of the response. For example, in FIGS. 4A and 4B, an initial slope of the response is illustrated. Based upon this initial slope, it is possible to extrapolate the value of $R_M$ without the necessity of allowing the heating to reach the maximum value. This technique can be used to increase the speed of the testing process. Further, this information can also be used to verify the value of $R_M$ detected by the sensor 122. For example, if the extrapolated value of $R_M$ differs significantly from the measured value of $R_M$, it may be an indication of a failing component, a damaged test strip, or some other error in the measurement. Further, as discussed above, the calibration information can be used to improve the accuracy of the measurements. For example, the calibration information can provide a baseline response to which the response signal is compared. Thus, the response threshold levels can be adjusted based upon the calibration information.

The energy source 220 can be any appropriate energy source. In one preferred embodiment, the energy source 220 comprises a laser. A variety of lasers are known in the art for use as a heat source and can be, for example, a continuous wave laser, pulsed wave laser or a reduced size laser. Thermal contrast sensitivity may be increased by using higher powered lasers and/or tuning the laser power for different concentrations of GNPs to extend the dynamic range. The laser can emit light in the visible range. Lasers may also be used that emit light in the near infrared region. Generally, the laser is selected and tuned to maximize the absorption within the nanoparticles while minimizing the interference from the background materials. The amount of laser power used in the LFA system can vary and is dependent on the components of the assay. In an exemplary embodiment, the laser power was between about 5W and about 50 W (continuous wave laser). However, higher or lower energy levels may be used in other embodiments. For instance, lower total energy but higher energy density may be applied with pulsed laser. With the reduction of background absorption discussed below, higher laser power maybe used for further improved sensitivity and signal strength.

Generally, the membrane, and backing include materials that have minimal light absorption. Background heating limits the ability to use higher energy to obtain higher signal strength. By selecting materials that have minimal light absorption, the background thermal reading can be reduced to ensure that the thermal detection is from the nanoparticles in the test region and not the materials of the assay system. The membrane in the LFA system is generally a porous material containing a plurality of interstices or pores. Liquid can flow through these interstices or pores generally by capillary action. The porous material can be made from natural or synthetic substances. Suitable porous materials for use in the LFA systems can include, for example, nitrocellulose, polyvinylidene fluoride (PVDF), polyethylene, nylon, cellulose acetate, polyester, polyethersulfone (PES), polysulfone and the like. Preferred embodiment uses the membrane that has the smallest light absorption. Other porous materials may also be used that are known in the art. A variety of backings are known in the art and mainly provide structural support for LFA. For thermal contrast detection, materials that have minimal light absorption are preferred as backing in the LFAs described herein. In one preferred embodiment, the backing can be made of glass or plastic (for instance polystyrene). Sample pad can be made from a variety of materials including, for example, polyester, polyacrylic, other polylmeric materials or glass fiber. Conjugate pad and absorbent pad can be made from, for example, cellulosic materials or the like.

Metallic nanoparticles generate heat upon optical stimulation. This heat generation results from surface plasmons at the metal-dielectric interface during transition from an excited to ground state. The amount of heat generated by GNPs, for example, can be described by the following equation:

$$Q = NQ_{nano} = NC_{abs}I \qquad \text{Equation (1)}$$

where the total heat generation (Q, W/m³) is the combined contribution of single GNP ($Q_{nano}$), written as the product of GNPs concentration (N, #/m³), GNP absorption cross section (m²), and laser intensity (W/m²).

The nanoparticles can comprise a variety of materials, shapes and sizes. The nanoparticles can be gold nanoparticles, silver nanoparticles, copper nanoparticles, platinum nanoparticles, aluminum nanoparticles, cadmium nanoparticles, composite particles, i.e. silver and gold, graphene nanoparticles and the like. In one preferred embodiment, the LFA assay system includes gold nanoparticles. Other types of nanoparticles may also be employed and are within the scope of this description. In alternative embodiments, a combination of two or more types of nanoparticles may be used. These may be used to identify multiple analytes or to amplify or enhance the signal.

The nanoparticles can include a range of sizes and generally must be able to travel through the membrane. Preferably, the diameter of the nanoparticles can be range from 10 nm to 200 nm. The selection and optimization of nanoparticle size depends partly on the energy absorption. For one preferred embodiment with laser as the energy source and gold nanoparticles, the physical phenomenon named plasmon resonance enhances the efficiency of optical absorption and therefore heat generation. Gold nanoparticles up to about 100 nm in diameter can be used. Larger sizes are available and may also be used and are included in the scope of the present invention. In some embodiments, GNPs with sizes of about 40-80 nm have the higher absorption efficiency (defined as $Q_{abs}=C_{abs}/A$, where Cabs is the absorption cross section and A is the projected cross sectional area of the particle) and are thus preferred from heat generation point of view.

A variety of shapes of nanoparticles can be used in the LFA system described herein and all are within the scope of the invention. The nanoparticles can be, for example, nanospheres, nanorods, nanoshells, nanocubes, nanourchins, nanopyramids, nanostars, and the like. In preferred embodiments, the nanoparticles are nanospheres, nanorods and/or nanoshells. Any of these shapes of nanoparticles can be used. The nanoparticles with the highest optical absorption efficiency and that can be functional in the assay with regards to other properties are preferable. For particles with nonspherical shape, effective radius (sphere with equivalent volume) may be used to calculate the absorption efficiency.

The polydispersity of the GNPs used in existing LFAs are not well controlled, as seen in FIGS. 12A-C and 13 for CrAg and hCG dipsticks. Better control of polydispersity leads to more uniform nanoparticles size distribution. This can lead to smaller standard deviations for thermal contrast detection, and therefore improves the signal stability and consistency. More uniform nanoparticles may also give higher optical absorption and heat generation. For instance, GNPs with different sizes have peak absorption at different wavelengths. For polydispersed GNP population, less GNPs will generate heat at peak absorption wavelength and thus reducing the amount of heat generated. In a sample of nanoparticles, well-dispersed nanoparticles of uniform size are preferable to nanoparticle clusters. Clustering of the nanoparticles can lead to less uniform absorption by the nanoparticles. The nanoparticles may, optionally, be coated to decrease clustering thereby increasing uniformity of absorption. The coating, if present, preferably does not reduce the absorption within the nanoparticles.

The size distribution of the nanoparticles can vary. In some embodiments, at least about 60 percent of the nanoparticles are within +/−10 nm of the mean diameter of the nanoparticles. Preferably, at least about 70 percent of the nanoparticles are within about +/−5 nm of the mean diameter of the nanoparticles. More preferably, at least about 70 percent of the nanoparticles are within about +/−3 nm of the mean diameter of the nanoparticles. Even more preferably, at least about 75 percent of the nanoparticles are within about +/−3 nm of the mean diameter of the nanoparticles. Nanoparticles outside of these ranges are also within the scope of the invention.

The amount or concentration of nanoparticles used in an LFA system can vary depending on the specific assay, the specific nanoparticles, the analyte binding molecules and the like. Generally, the amount of nanoparticles can be on the order of about 1-100 μg. Nanoparticle amounts outside of this range may also be used and are within the scope of this invention. For one embodiment, CrAg assay uses about 4 μg of GNPs per LFA. The amount of nanoparticles used can be higher or lower than the specified range depending on binding affinity of the binding molecules, concentration range of target analyte in the patient samples, among other factors Analytes in a variety of samples may be determined and generally can be any type of liquid sample. The samples may be biological samples, chemical samples, environmental samples, food samples and the like. Biological samples can include, for example, blood, plasma, serum, urine, sweat, bile, cerebrospinal fluid, fecal material, vaginal fluids, saliva and the like. Other biological samples may also be analyzed and are all within the scope of this invention. The sample with the analyte may be used directly or diluted using diluent. Diluent can be a variety of solutions and are generally known in the art. In an exemplary embodiment, the diluent is a saline solution.

A variety of analytes can be detected using the methods and devices of the present description. A target analyte can be a protein, peptide, nucleic acid, hapten, chemical and the like. Analytes can also include therapeutic drugs, drugs of abuse, hormones, vitamins, glucose proteins, antibodies, steroids, bacteria or bacterial infection, fungi, viruses, parasites, components and products of bacteria, allergens, antigens and the like. An analyte can also include derivatives or metabolites of the compound of interest.

In some embodiments, the analyte can be associated with a disease, for example, malaria, TB and the like. In other embodiments, the analyte can be associated with a physiological or pathological condition, for example, pregnancy. Examples of analytes include Cryptococcal antigen (CrAg), malarial antigen, Tuberculosis antigen, human chorionic gonadotropin (hCG), human luteinizing hormone (hLH), human follicle stimulating hormone (hFSF), prostate speific antigen (PSA), hepatitis B surface antigen, hepatitis B antibodies, HIV antigen, *Streptococcus* A, *Staphylococcus* bacteria, STDs, *P. Falciparum*, Fever panel and the like.

The analyte binding molecules and the capture molecules can be any molecule that is capable of binding the target analyte. In some embodiments, the analyte binding molecules and the capture molecules are biological macromolecules, for example, antibodies or parts of antibodies. These molecules can also be receptors, ligands, polynucleotides, polypeptides, glycopeptides, lipoproteins, nucleoproteins, nucleic acid, aptamer, and the like. In one exemplary embodiment, the analyte binding molecules and the capture molecules are antibodies. In some embodiments, the analyte binding molecules are the same as the capture molecules. In other embodiments, the analyte binding molecules are different than the capture molecules.

A variety of methods are known in the art to conjugate or couple the nanoparticles to the analyte binding molecules and all are within the scope of this invention. Generally, conjugation chemistry that allow improved stability at high temperatures, high or low humidities and/or radiative conditions are preferable. Chemical binding refers to the use of chemical functional groups and/or molecules that link the particles to the analyte binding molecule. An example is the placement of carboxylic acids on the surface of the particles to allow for linkage to amine functional groups on an antibody through a carbodiimide mediated molecule. Conjugation may involve passive adsorption. Passive adsorption is known in the art and disclosed, for example in US 2010/0136566 incorporated herein by reference.

A variety of liquid dispensing and spray technologies are known in the art for deposition of the capture molecules to the membrane. Any of these may be used and spray technologies that lead to better absorption and stability of the capture molecules are preferable. Nanoparticles conjugated to analyte binding molecules may also be sprayed onto the conjugate pad. In an exemplary embodiment, a variety of liquid dispensing instruments from BioDot™ may be used for these purposes.

The present description also includes a method of detecting an analyte in a sample. The LFA analytical sensitivity can be substantially improved, potentially >10.000-fold over visual detection methods by the use of thermal contrast technology described herein.

The method includes contacting a sample with the sample pad and allowing the liquid to flow through the membrane by capillary action. Nanoparticles conjugated with the analyte binding molecules move within the membrane through capillary action in response to the sample application. When present, the target analyte binds to the conjugated nanoparticles. The nanoparticle/analyte complex stops moving though the membrane when the capture molecule in the test region recognizes and binds the nanoparticle/analyte complex. This leads to accumulation of the nanoparticle/analyte complex at the test zone or region of the LFA. The method further includes using the thermal contrast reader to detect and quantitate the amount of analyte in the test region by first exposing the test region to an energy source such as a laser and then measuring the heat generated from the test strip by a sensor. The output generated by the sensor is indicative of the presence and/or amount of the target analyte.

The method can also include detecting multiple analytes. Multiple analytes can be detected by having multiple test regions, wherein each test region has different capture molecules. Thus, the first nanoparticle/analyte complex binds to test region 1 having a first capture molecule that binds the first analyte, wherein the second nanoparticle/analyte complex binds to test region 2 having a second capture molecule that binds the second analyte and not the first analyte. In this manner, the LFA system can be extended to identify multiple analytes by configuring to include multiple test regions. Multiple analytes may also be detected using multiple nanoparticles having differing starting positions. The nanoparticles may have different conjugates and different analyte binding molecules. These can be tuned to have different flows through the membrane. The multiple analytes may be in the same sample or different samples. In some embodiments, multiple analytes may be tested in the same test region. The detection of the multiple analytes results in the identification, preferably with a quantitative amount of analyte, for each of the analytes in the corresponding test region. In some embodiments, the multiple analytes may also be detected and/or quantified cumulatively in one test region. For example, using different particles that absorb at different laser wavelengths allows multiplexing using laser excitation with corresponding wavelengths.

The method can also include amplification of the signals through the use of a secondary controlled flow of different nanoparticles. In one exemplary embodiment, the signal from a LFA with primary gold nanoparticles can be amplified by the use of silver staining or secondary binding nanoparticles. In the process of silver staining, the gold nanoparticles can act as a nucleation site for the growth of a silver shell on the surface. In the process of secondary nanoparticle binding, the secondary nanoparticle binds to the first particle that captures the target analyte to amplyify the signal.

The present method also includes quantitation of the amount of analyte present in the test region. The measurement of the thermal change of the membrane can be correlated to the amount of analyte present in the test region. The LFA system can advantageously provide not only the presence or absence of analyte but also provides the level of analyte present in the membrane and consequently the sample. This is particularly advantageous for determining the extent of the disease, infection or condition in a patient.

After the test region is exposed to an energy source, the presence and amount of analyte can be detected by measuring the thermal change or temperature in the test region of the membrane. Alternatively, the initial rate of temperature change can also be measured to determine the specific absorption rate (SAR). SAR can be used to determine the amount of analyte present in the test region. SAR is in effect the Q in Equation 1 above. It relates to the amount of heat energy in $W/m^3$ given off by the nanoparticles once they have been activated by an energy source such as a laser. As shown in Equation 1, it is directly proportional to the laser fluence and the number of nanoparticles which then relates directly to the amount of antigen in the analyte.

Aside from the improvement in the analytical sensitivity, the LFAs can also be archived for future analysis. Unlike other detection methods, there is no loss of signal using the thermal contrast system. In fluorescence measurements, organic fluorophores experience photobleaching. In some colorimetric measurements, the dyes may lose their signal over time through photodestruction. Thermal contrast readings conducted after two weeks of conducting the assay can be nearly identical. This advantageously allows for processing point-of-care LFAs in the field and referral to a central lab to process the same LFA system for thermal contrast readings. In other words, the analyte signal does not have to be measured immediately after the sample is run. The signal may be measured multiple times, for example, immediately after the assay is complete and also at a later time. The method can also include exposing the test region to the energy source and measuring the analyte in the test region after twelve hours, 24 hours or more after contacting the assay strip with the sample.

Cryptococcosis is among the leading causes of death among all AIDS-related opportunistic infections and is the most common cause of meningitis in adults in Africa causing >500,000 deaths worldwide annually. Cryptococcal meningitis is classically diagnosed by a combination of culture, India ink, or CrAg testing with semi-quantification by serial two-fold dilutions (i.e. CrAg titer, defined as the last positive test when performing two-fold serial dilutions).

The present description includes a method for detection and quantification of the CrAg antigen. The method includes contacting a sample with the sample pad and allowing the liquid to flow through the membrane by capillary action. Nanoparticles conjugated with the CrAg binding molecules move within the membrane through capillary action in response to the sample application. When present, the CrAg binds to the conjugated nanoparticles. The nanoparticle/CrAg complex stops moving though the membrane when the capture molecule in the test region recognizes and binds the nanoparticle/CrAg complex. This leads to accumulation of the nanoparticle/CrAg complex at the test region of the LFA. The thermal contrast system can be used to detect and quantitate the amount of CrAg in the test region by first exposing the test region to a heat source such as a laser and then measuring the heat generated from the test strip by a heat sensor.

Figure 6:
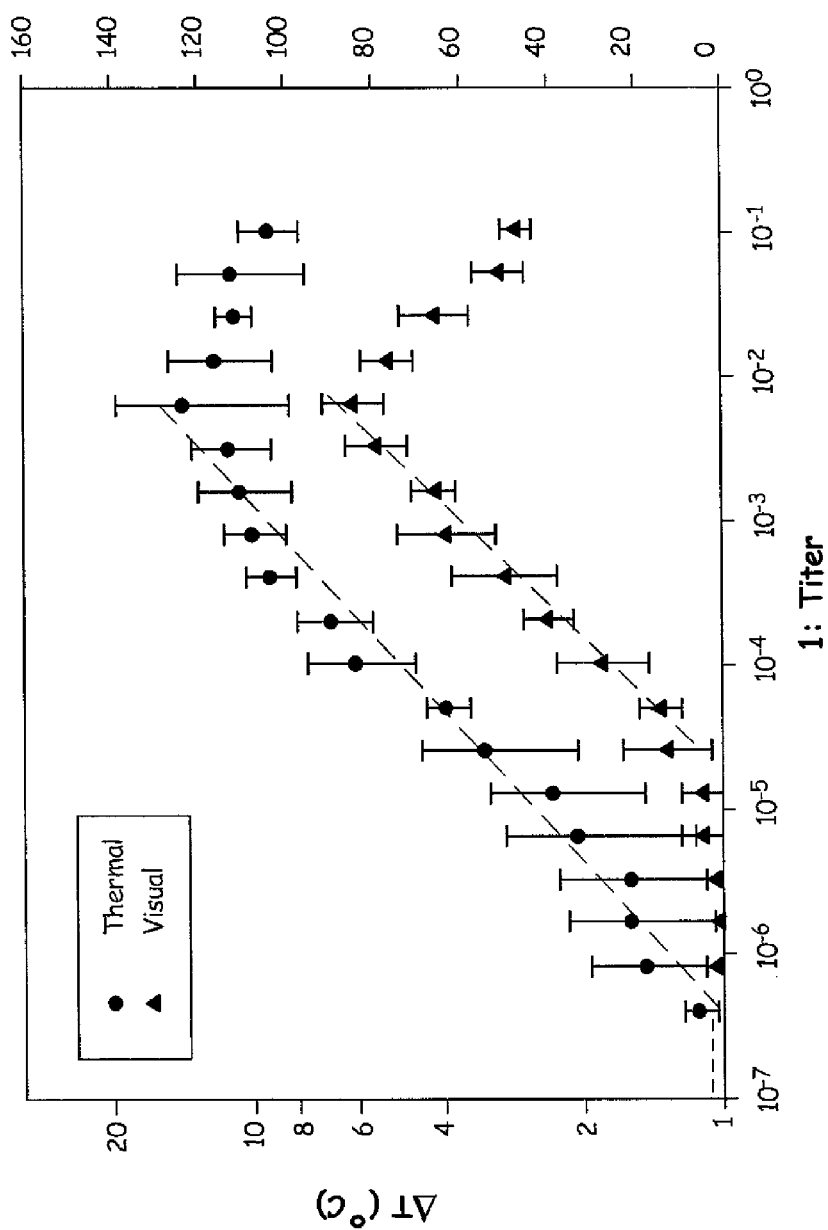
FIG. 6 is a graph that illustrates how thermal contrast enhances the detection of existing immunochromatographic lateral flow assays for cryptococcal antigen (CrAg). The plateau of signal at high concentrations is due to the high dose hook effect of the LFA. The dashed line shows background from the control sample.

FIG. 6 shows thermal contrast produced a 32-fold greater improvement in the analytical sensitivity than colorimetric detection with a log-linear slope up to an equivalent concentration of 1:1024 CrAg titer by latex agglutination ($R^2=0.98$). Above this 1:1024 titer, there was a high dose "hook" effect with decreased visual intensity and a plateau of thermal intensity. This can be overcome either by changing the dilution of the assay, or changing the engineering of the assay. In addition, the inter-assay precision of the assay can be improved by standardizing the size of these nanoparticles to decrease the coefficient of variance. For comparison, the median CrAg titer observed in patients with cryptococcal meningitis is often 1:1024 to 1:2048. However, there is a sub-acute onset over weeks to months with CrAg titers >1:8 in asymptomatic persons with subclinical disease predictive of later development of cryptococcal meningitis with 100% sensitivity and 96% specificity despite HIV therapy. Serum CrAg screening and preemptive antifungal treatment in persons living with advanced AIDS aborts the clinical progression to symptomatic meningitis. Non-invasive screening is possible with CrAg being detectable in urine, but urine has 22-fold lower CrAg concentration than blood. Thus, improvement in LFA sensitivity by thermal contrast can enable non-invasive screening of asymptomatic persons with AIDS, and the ability to quantify CrAg burden to risk stratify.

The present description includes a method for detection and quantification of the hCG antigen. The method includes contacting a sample with the sample pad and allowing the liquid to flow through the membrane by capillary action. Nanoparticles conjugated with the hCG binding molecules move within the membrane through capillary action in response to the sample application. When present, the hCG binds to the conjugated nanoparticles. The nanoparticle/hCG complex stops moving though the membrane when the capture molecule in the test region recognizes and binds the nanoparticle/hCG complex. This leads to accumulation of the nanoparticle/hCG complex at the test region of the LFA. The thermal contrast system can be used to detect and quantitate the amount of hCG in the test region by first exposing the test region to a heat source such as a laser and then measuring the heat generated from the test strip by a heat sensor.

The present description includes a method for detection and quantification of the malaria antigen. The method includes contacting a sample with the sample pad and allowing the liquid to flow through the membrane by capillary action. Nanoparticles conjugated with the malaria antigen binding molecules move within the membrane through capillary action in response to the sample application. When present, the malaria antigen binds to the conjugated nanoparticles. The nanoparticle/malaria antigen complex stops moving though the membrane when the capture molecule in the test region recognize and bind the nanoparticle/malaria antigen complex. This leads to accumulation of the nanoparticle/malaria antigen complex at the test region of the LFA. The thermal contrast system can be used to detect and quantitate the amount of malaria antigen in the test region by first exposing the test region to a heat source such as a laser and then measuring the heat generated from the test strip by a heat sensor.

The present description includes a method for detection and quantification of the TB antigen. The method includes contacting a sample with the sample pad and allowing the liquid to flow through the membrane by capillary action. Nanoparticles conjugated with the TB antigen binding molecules move within the membrane through capillary action in response to the sample application. When present, the TB antigen binds to the conjugated nanoparticles. The nanoparticle/TB antigen complex stops moving though the membrane when the capture molecule in the test region recognizes and binds the nanoparticle/TB antigen complex. This leads to accumulation of the nanoparticle/TB antigen complex at the test region of the LFA. The thermal contrast system can be used to detect and quantitate the amount of TB antigen in the test region by first exposing the test region to a heat source such as a laser and then measuring the heat generated from the test strip by a heat sensor.

EXAMPLES

Example 1

Synthesis and Analysis of GNPs

Gold nanoparticle (GNP) synthesis: 30 nm GNPs were synthesized by citrate reduction of chloroauric acid and then coated with polyethylene glycol (PEG) to maintain stability in aqueous solutions as described in Frens G., Perault et al. and Neha et al. (See Frens G. Nat. Phys. Sci. 1973; Perrault, Steven D. et al. Nano Letters 2009 9 (5) 1909-1915; Neha B. Shah et al. Molecular Pharmaceutics 2012 9 (8) 2146-2155. Characterizations of GNPs by UV-Vis spectrophotometer, atomic emission spectroscopy, dynamic light scattering and TEM were performed to ensure the success of the synthesis and quantify concentration and size. Titrated concentrations of GNP water solutions were prepared and 10 µL of each solution was transferred to a glass slide as a drop. Laser beam from a CW Laser (532 nm, Millennia Vs, Diode pumped) then irradiated the drop for 1 minute, thereby inducing GNP heat generation. An infrared camera (FLIR ThermoVision™ A20) mounted at an angle above the sample measured temperature change remotely during laser irradiation. The maximum temperature change for each sample was determined from the thermal images and plotted.

The thermal contrast versus visual contrast of GNPs in solution was compared. A series of different concentrations of GNPs were prepared. 10 µL of the GNP solution was placed on a microscope slide. For visual analysis, a picture was taken by a digital camera and analyzed later with Image J. For thermal analysis, the GNP solution was irradiated with laser (0.5 W, 532 nm) and the temperature change was recorded by an infrared camera.

Figure 5:
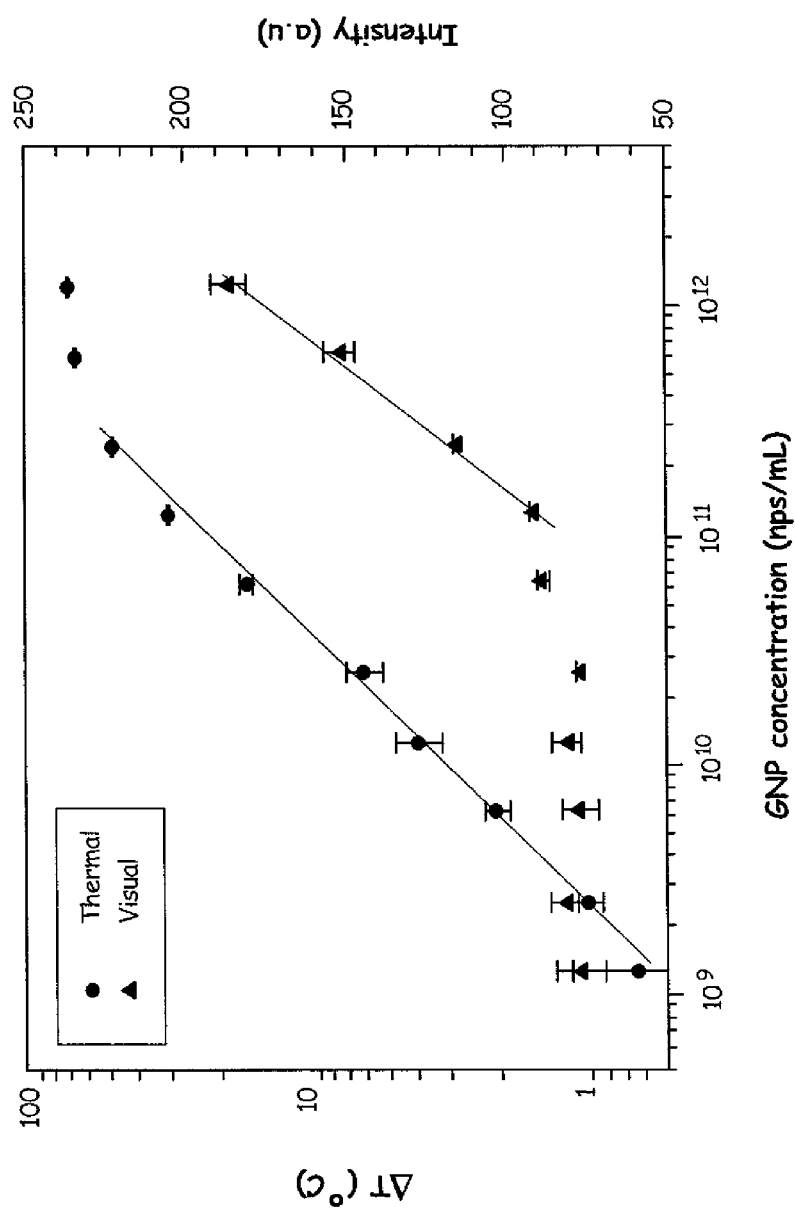
FIG. 5 is a graph illustrating the use of gold nanoparticles (GNPs) in a thermal contrast assay.

The results showed that GNPs can be detected down to $2.5 \times 10^9$ nanoparticles/mL of GNPs using thermal contrast in comparison to $2.5 \times 10^{11}$ nanoparticles/mL by visual contrast. This clearly demonstrated that thermal contrast for detection can improve the overall analytical sensitivity by 100-fold (FIG. 5). The thermal contrast of GNPs was also compared with standard optical density measurement using a standard micro-volume plate reader, the principle of which is widely used in microfluidic ELISA. With the same sample volume (10 µL), the thermal contrast displayed 50-fold improvement over the optical density measurement. Further improvement in thermal contrast sensitivity can be possible by using higher powered lasers and/or tuning the laser power for different concentrations of GNPs to extend the dynamic range of thermal contrast. Importantly, by tuning laser wavelength to a higher absorbing nanoparticle (gold nanorod) we may also be able to increase the sensitivity.

Example 2

Detection of the Cryptococcal Antigen (CrAg)

The analytical performance of thermal contrast versus colorimetric detection (i.e. visual contrast) was tested using FDA-approved LFAs for detecting cryptococcal antigen (CrAg) obtained from Immy, Inc. and described in Qin et al. Angewandte Chemie 2012. Thermal contrast imaging of LFAs: Cryptococcal antigen LFA (Immy, Inc. Norman, Okla.), which was FDA-approved in July 2011, detects the capsular polysaccharide antigens of *Cryptococcus* species complex (*Cryptococcus neoformans* and *Cryptococcus gattii*) in serum and cerebrospinal fluid (CSF). A serum sample from a patient with cryptococcal meningitis had 2-fold serial dilutions performed to assess the limits of detection, as the CrAg titer. The test was conducted following the manufacturer's instructions. Thermal contrast was performed by irradiating the test line by laser for 1 minute. An infrared camera recorded temperature change. Three spots on each horizontal test band were irradiated and the average maximum temperature change was measured. At each concentration, three separate LFA dipsticks were run. The results are shown in FIG. 6.

Visual contrast quantification: For the GNP droplets, images were taken by a digital camera. The dipsticks were scanned by a flatbed scanner (Model: Visioneer Onetouch 7400). The mean grey intensity for regions of interest (ROI). i.e. droplet and the test band for dipsticks, was analyzed. The same volume of GNP solution (10 µL) was also measured by a spectrophotometer at 530 nm, with a Take3 micro-volume plate and Synergy HT Multi-Mode Microplate Reader (BioTek, Winooski, Vt.).

The LFA serial 2-fold dilutions of a serum sample, positive at 1:32768 titer by latex agglutination (Immy, Inc.) were compared. Results showed that thermal contrast was indeed more sensitive than colorimetric visual detection on the LFA. FIG. 6 shows thermal contrast produced a 32-fold greater improvement in the analytical sensitivity than colorimetric detection with a log-linear slope up to an equivalent concentration of 1:1024 CrAg titer. Above this 1:1024 titer, there was a high dose "hook" effect with decreased visual intensity and a plateau of thermal intensity.

Using FDA-approved cryptococcal antigen (CrAg) LFAs, a 32-fold improvement in analytical sensitivity with thermal contrast was seen (FIG. 6) while simultaneously quantifying the antigen concentration. This enhanced sensitivity in a "disposable RDT with a reader" model can enable CrAg screening and quantification in resource-limited areas for both symptomatic and asymptomatic CrAg+ allowing targeted preemptive antifungal therapy in patients previously undetected by the qualitative LFAs.

Example 3

Improving Analytical Sensitivity of LFAs

Figure 7A:
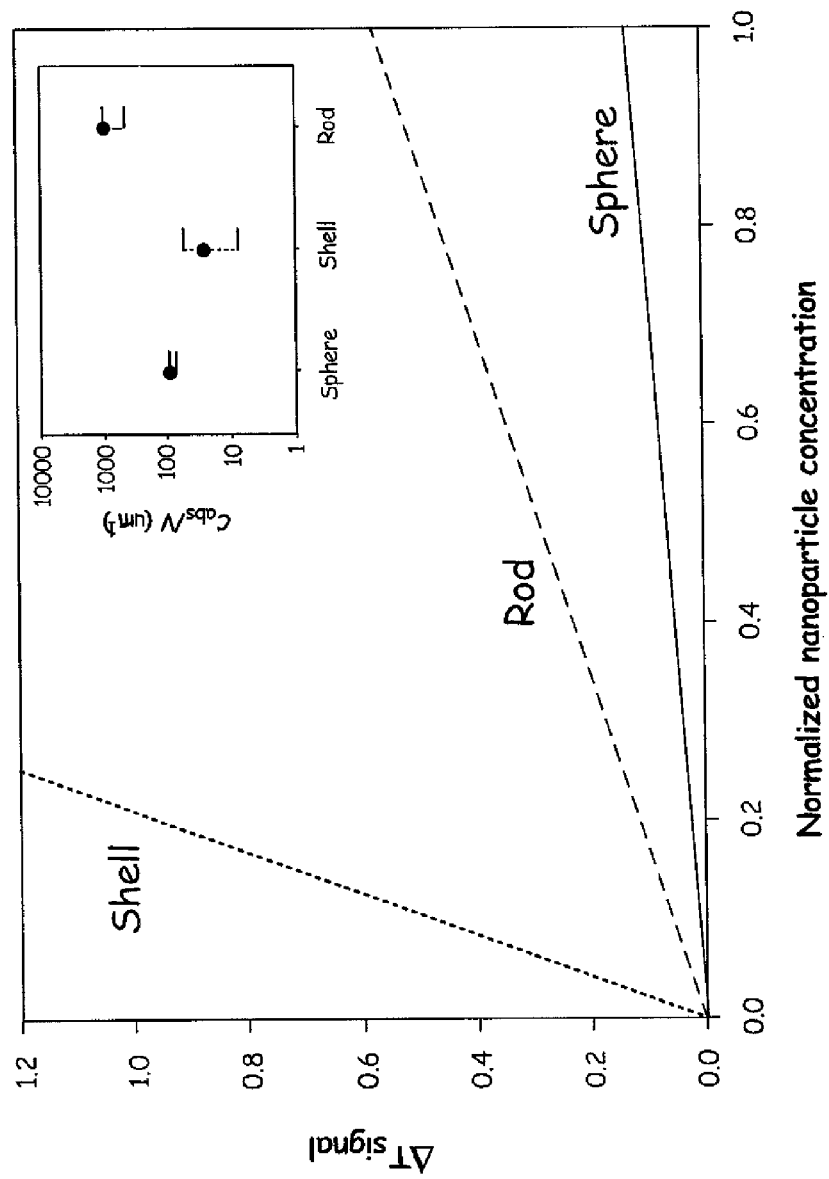
FIG. 7A is a graph of nanoparticle concentration versus temperature change for different nanoparticle shapes.
Figure 7B:
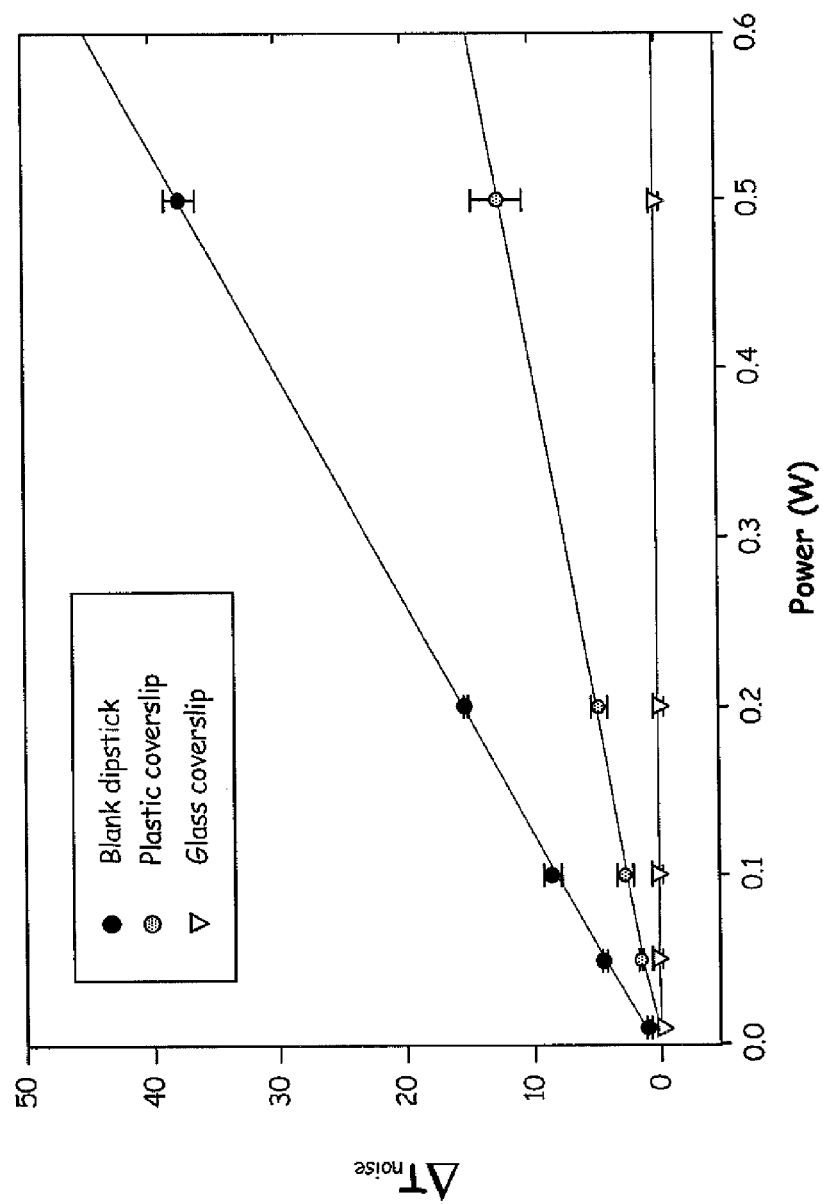
FIG. 7B is a graph of temperature change for different materials.

Modeling was conducted based on experimentally measured absorption cross sections of a variety of gold nanoparticles such as rods, shells and spheres to explore further improvement of the analytical sensitivity of LFAs. Gold nanoparticles including gold nanorods, nanoshells, and gold nanospheres were evaluated. As shown in FIG. 7A, at the equivalent laser power and nanoparticle concentration, typical nanorods and nanoshells generate 4.6-fold and 36-fold more heat than gold nanospheres, respectively. To eliminate the particle size effect, the absorption cross section ($C_{abs}$) was normalized by particle volume (V) to give a better assessment of the heat generation capability. The sizes of the GNPs used for this comparison were: sphere D=30 nm, nanorod D=12.7 nm by L=49.5 nm, and nanoshell $D_{core}$=120 nm (silica), $D_{shell}$=150 nm (gold). The thermal contrast ($\Delta T_{signal}$) and nanoparticle concentrations are normalized. Using this normalization, gold nanorods were about one order of magnitude more efficient in heat generation than the gold nanospheres and nanoshells (FIG. 7A inset). In addition, current LFAs (i.e. thin nitrocellulose membranes with thick backing material) absorb significant amounts of laser energy (at 532 nm) creating background heating or noise. Thus, use of low absorbing (i.e. high transmitting or reflective) backing materials, such as plastic or glass, allows the use of higher laser intensities (I). Substrate absorption: A blank dipstick and plastic and glass cover glasses were irradiated with 532 nm laser for 1 minute each. The temperature change during laser irradiation was measured by infrared camera and the maximum temperature change determined. (See FIG. 7B) Combining higher absorbing nanoparticles and low absorbing LFA backing materials can increase the sensitivity. It is worth noting that the gold nanorod may absorb efficiently at different wavelength than the gold nanosphere.

A 1000-fold further increase in thermal contrast can be produced by increasing the power density by 100 times (i.e., increase in laser power from 0.01 to 1 W) and using a nanoparticle with a 10-fold increase in absorption ($C_{abs}$). Higher laser powers can be used by reducing background absorption discussed above.

The analytical sensitivity of the assays can be improved by about 10,000 fold, considering the over 10 fold improvement shown and 1000 fold improvement predicted above over visual detection methods using the modifications described here.

Example 4

Detection of hCG

The presence of hCG (pregnancy test) in a sample was tested using a LFA with the GNPs. The hCG LFA was purchased from Fisher Scientific (Sure-Vue Serum/Urine hCG test kit).

Figure 8A:
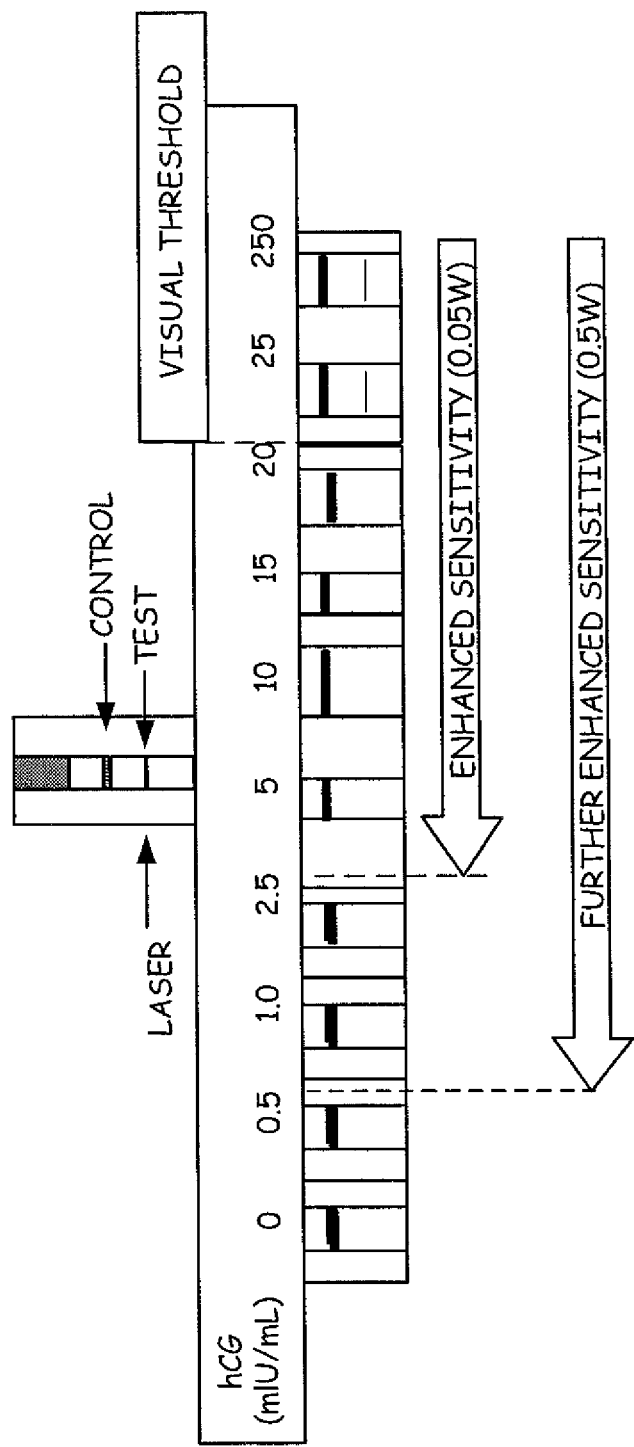
FIG. 8A is a schematic representation of a picture of results from thermal contrast assay for hCG (Human chorionic gonadotropin).
Figure 8B:
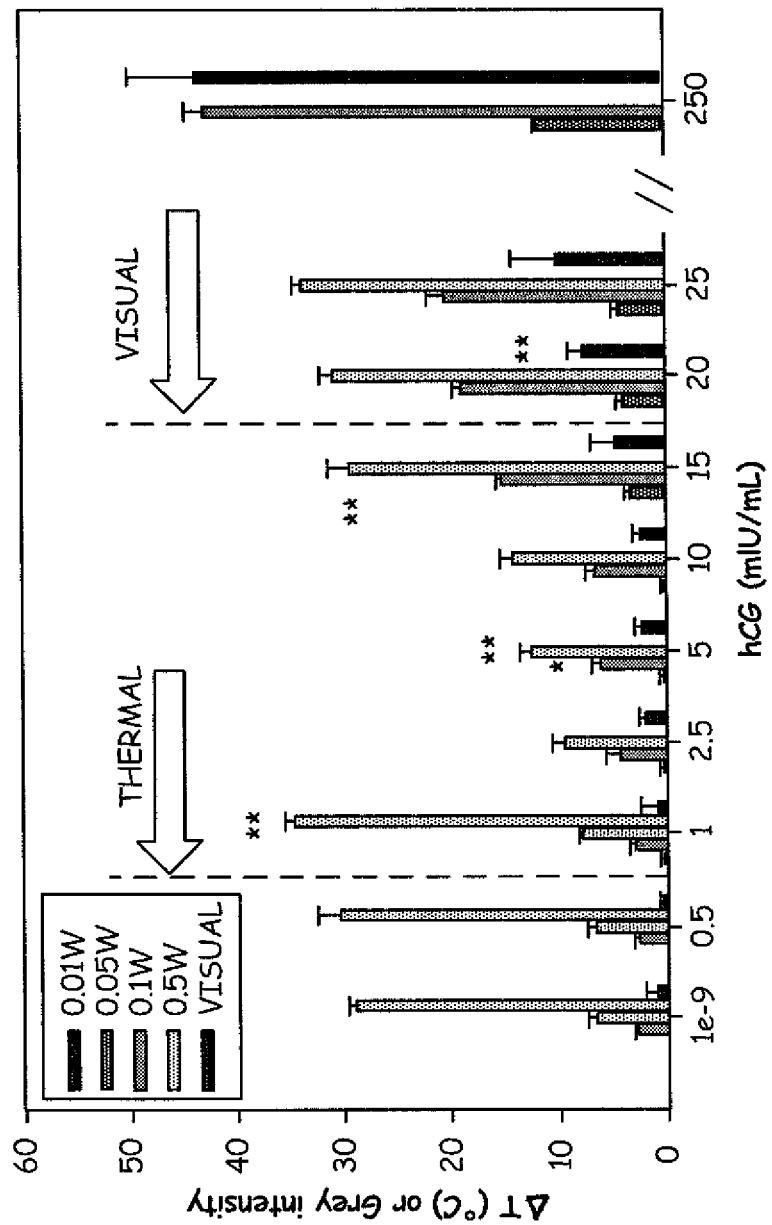
FIG. 8B is a graph of results from thermal contrast assay for hCG.

As shown in FIG. 8A and FIG. 8B, thermal contrast showed enhanced sensitivity to the presence of hCG relative to visual detection. The use of thermal contrast showed a 20-fold increase in the limit of detection.

Example 5

Detection of Malaria

The presence of the malaria antigen was also tested using a LFA with the GNPs. Malaria LFA was purchased from Alere Inc (BinaxNOW™ malaria test).

Figure 9:
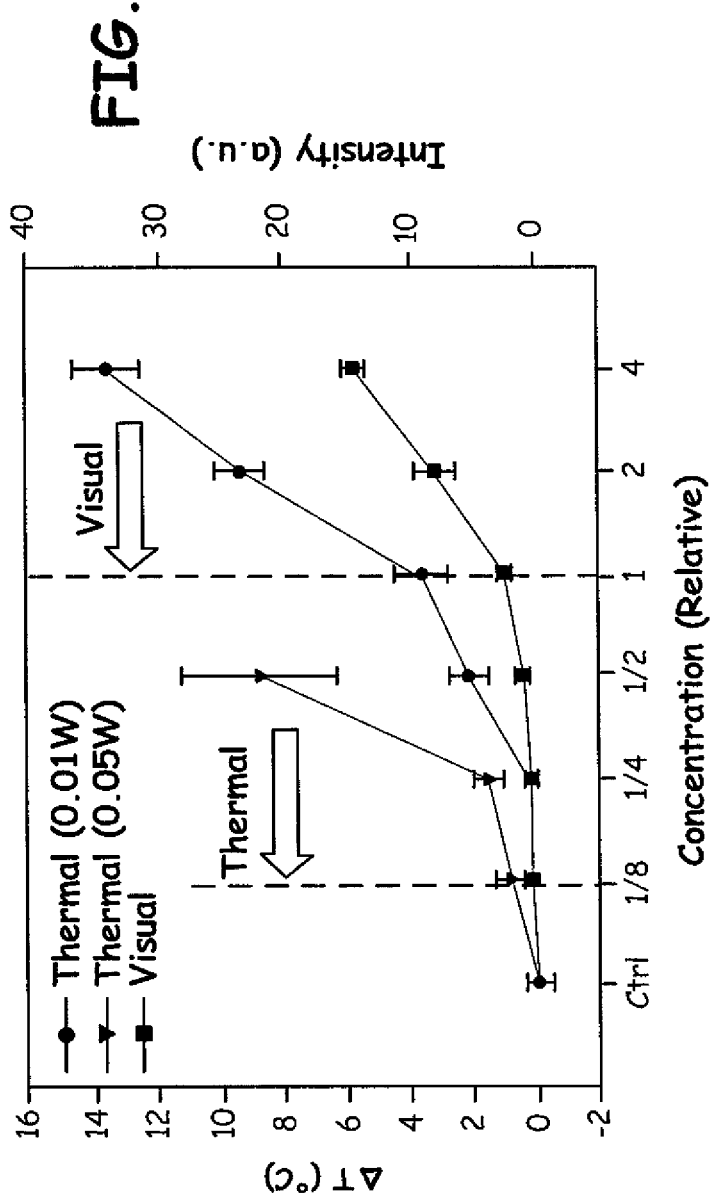
FIG. 9 is a graph of results from thermal contrast assay for malaria antigen.

As shown in FIG. 9, thermal contrast showed enhanced sensitivity to the presence of the malaria antigen relative to visual detection. The use of thermal contrast showed an 8-fold increase in the limit of detection.

Example 6

Detection of TB

The presence of TB was tested using a LFA with the GNPs. TB LFA was manufactured by Alere Inc (Determine™ TB LAM rapid test). The results are shown in Table 1. Thermal contrast detects a majority of visually negative TB LFAs (i.e. false negatives) based on reference standard of a sputum culture.

TABLE 1

| Method | Ratio Detected | Percent Detected |
|---|---|---|
| TB-LAM LFA - visual | 0/39 | 0 |
| TB-LAM LFA - thermal | 22/39 | 56 |
| Sputum Culture | 39/39 | 100 |

This directly speaks to the increase in sensitivity of the test since thermal contrast reduces the false negative test results.

Example 7

Use of Specific Absorption Rate for hCG

This experiment was conducted to see if the thermal contrast can be performed using the specific absorption rate (SAR). The thermal contrast in Examples 1-7 were performed based on ΔT. The SAR is based on the initial slope of the temperature change.

Figure 10A:
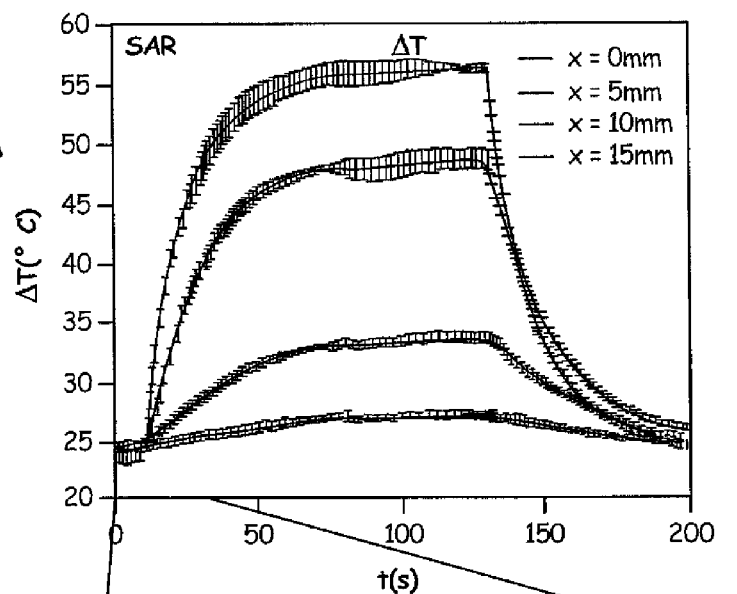
FIG. 10A and FIG. 10B are graphs illustrating the use of SAR.
Figure 10B:
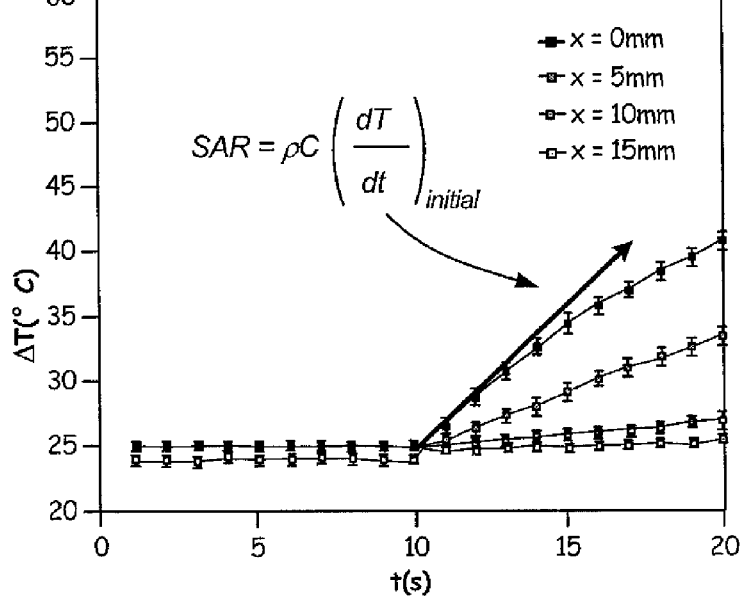
Figure 11:
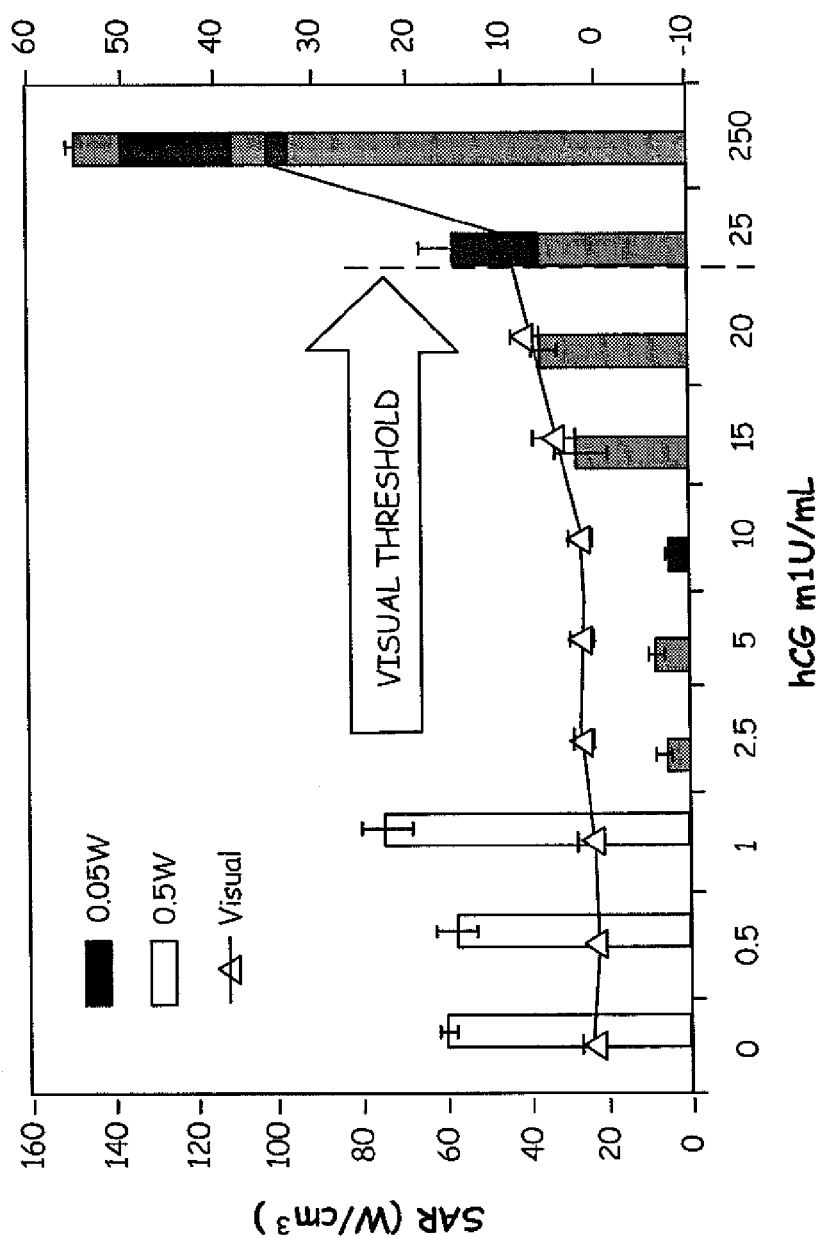
FIG. 11 is a graph of results from thermal contrast assay for hCG using SAR.

FIG. 10A shows the temperature change over an extended period of time. FIG. 10B illustrates the change in temperature in the first 20 seconds. As shown in FIG. 10A and FIG. 10B, thermal contrast can be conducted by calculating the SAR. This enables the measurement at an earlier time to minimize interference. Specifically, heat addition over time leads to diffusion in a material. If the heat can be added very quickly such that diffusion is minimized, then the rate of temperature change is related entirely to the SAR (or Q in Equation 1) and therefore can more directly capture the presence of the GNPs and thus antigen in the test. This may allow the use of a pulsed laser. FIG. 11 illustrates the results from an experiment in using hCG as described above in Example 4 except the SAR was determined instead of the temperature change. As can be seen, SAR can be used for detection of analytes without a loss of sensitivity or accuracy.

Example 8

Use of Monodisperse Particles

The nanoparticles were made as described in Example 1 using the method of Frens and analyzed for dispersity.

Figure 12C:
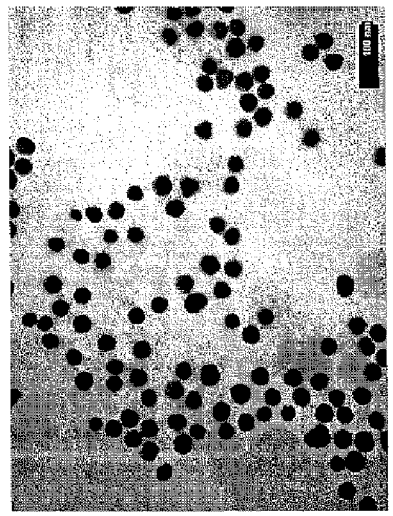
FIGS. 12A, 12B and 12C are pictures showing the polydispersity of GNPs in CrAg dipstick, hCG dipstick and synthesized GNPs, respectively.
Figure 12B:
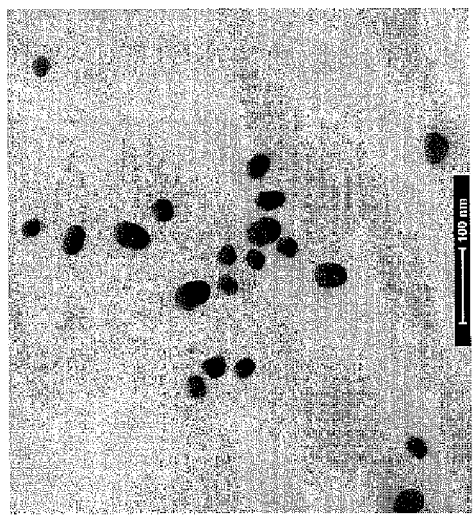
Figure 12A:
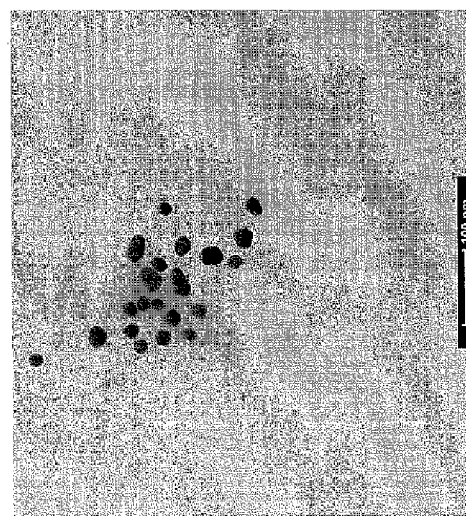

As can be seen in FIG. 12A, FIG. 12B and FIG. 12C, the synthesized GNPs are more evenly dispersed than the GNPs in the dipsticks.

Figure 13:
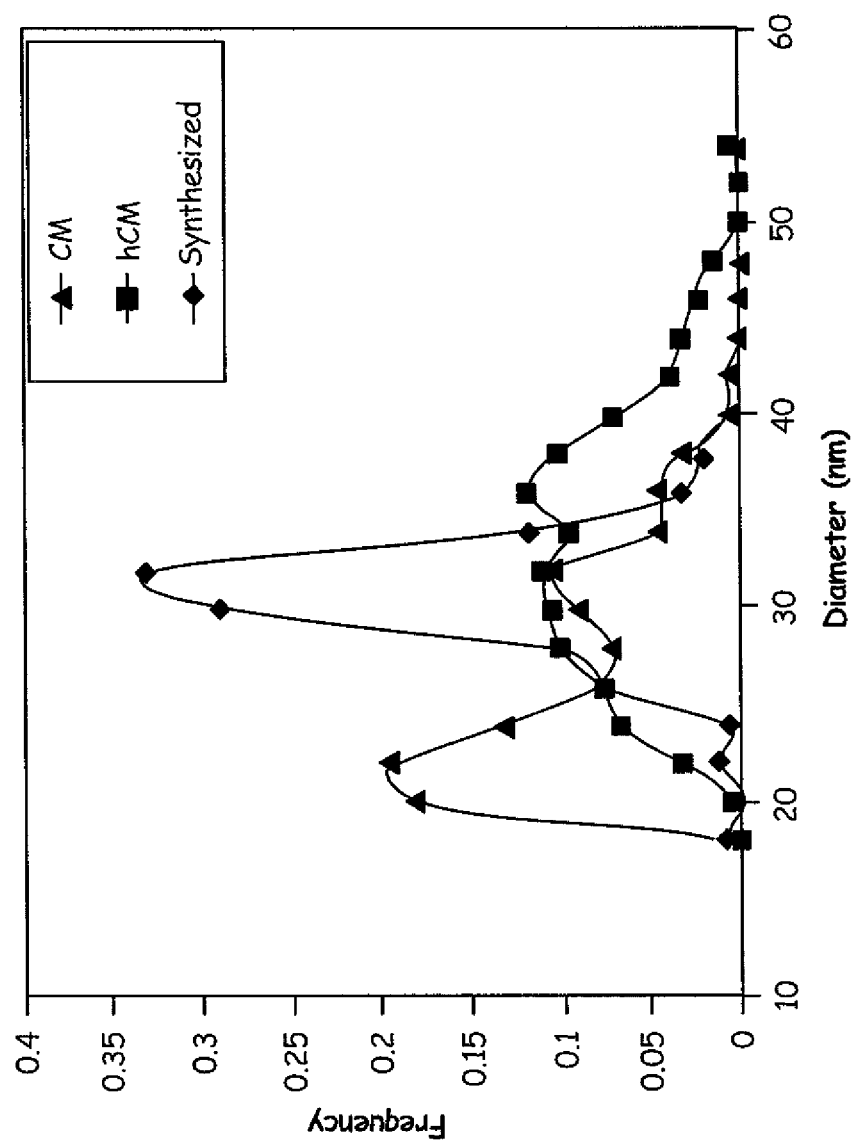
FIG. 13 is a plot of illustrating the uniform size of the synthesized GNPs.

FIG. 13 is a quantification of the results seen in the TEM images of FIG. 12. Specifically, the counts of GNPs of different sizes are added and the graph illustrates that there is a much broader distribution within the existing dipsticks vs. those synthesized by the method of Frens.

Although the present invention has been described with reference to preferred embodiments, workers skilled in the art will recognize that changes may be made in form and detail without departing from the spirit and scope of the invention.

What is claimed is:

1. A thermal contrast assay reader comprising an energy source, a sensor, I/O circuitry and an opening to receive an assay strip, the reader configured to convert the sensor results to an output signal upon activation of the energy source onto the test region of the assay strip, wherein the sensor is an infrared sensor configured to measure thermal contrast in the test region of the assay strip.

2. The reader of claim 1 wherein the energy source is a laser.

3. The reader of claim 1 wherein the infrared sensor is an infrared camera.

4. The reader of claim 1 wherein the test region of the assay strip comprises nanoparticles.

5. The reader of claim 1 wherein the reader is a bench-top device and the output signal is displayed on a display on the bench-top device.

6. The reader of claim 1 wherein the reader is a handheld device and the output signal is displayed on a display on the handheld device.

7. The reader of claim 1 wherein the output signal is transmitted to another device through a wired connection.

8. The reader of claim 1 wherein the output signal is transmitted to another device through a wireless connection.

* * * * *

UNITED STATES PATENT AND TRADEMARK OFFICE
CERTIFICATE OF CORRECTION

PATENT NO.         : 9,651,508 B2
APPLICATION NO.    : 14/375294
DATED              : May 16, 2017
INVENTOR(S)        : John C. Bishof et al.

Page 1 of 1

It is certified that error appears in the above-identified patent and that said Letters Patent is hereby corrected as shown below:

On the Title Page

Please insert the following:
--Related U.S. Application Data
(60) Provisional application No. 61/593,036, filed on Jan. 31, 2012.--

Signed and Sealed this
Sixth Day of February, 2018

Joseph Matal
*Performing the Functions and Duties of the*
*Under Secretary of Commerce for Intellectual Property and*
*Director of the United States Patent and Trademark Office*